United States Patent [19]

Babiuk et al.

[11] Patent Number: 5,151,267

[45] Date of Patent: Sep. 29, 1992

[54] BOVINE HERPESVIRUS TYPE 1 POLYPEPTIDES AND VACCINES

[75] Inventors: Lorne Babiuk; Sylvia van den Hurk, both of Saskatoon, Canada; Tim Zamb, Lincoln, Nebr.; David Fitzpatrick, Saskatoon, Canada

[73] Assignee: University of Saskatchewan, Saskatoon, Canada

[21] Appl. No.: 219,939

[22] Filed: Jul. 15, 1988

[51] Int. Cl.⁵ .................. A61K 39/12; C07K 7/06; C07K 7/08; C12N 7/00

[52] U.S. Cl. .................... 424/89; 530/395; 530/403

[58] Field of Search .............. 530/395, 403; 424/89

[56] References Cited

U.S. PATENT DOCUMENTS

| | | | |
|---|---|---|---|
| 4,335,105 | 6/1982 | Gough | 530/395 |
| 4,341,784 | 7/1982 | Kaplan et al. | 530/395 |
| 4,642,333 | 2/1987 | Person | 424/89 |
| 4,661,349 | 4/1987 | Kino et al. | 424/89 |
| 4,680,176 | 7/1987 | Berns et al. | 424/89 |
| 4,709,011 | 11/1987 | Cohen et al. | 424/89 |
| 4,724,146 | 2/1988 | Kino et al. | 424/89 |

FOREIGN PATENT DOCUMENTS

| | | | |
|---|---|---|---|
| 0362531 | 4/1990 | European Pat. Off. | 530/395 |
| 8802634 | 4/1989 | PCT Int'l Appl. | 424/89 |
| 1390468 | 3/1973 | United Kingdom | 424/89 |

OTHER PUBLICATIONS

Mayfield et al., (1983), J. Virol., 47:259–264.
Pachl et al., (1987), J. Virol., 61:315–325.
Babiuk et al., (1987), Virology, 159:57–66.
van Drunen Littel-van den Hurk et al., (1985), Virology, 144:204–215.
van Drunen Littel-van den Hurk et al., (1986), J. Clin. Microbiol., 23:274–282.
Okazaki et al., (1987), Arch. Virol., 92:17–26.
van Drunen Littel-van den Hurk et al., (1985), Virology, 144:216–227.
Collins et al., (1984), J. Virol., 52:403–409.
Okazaki et al., (1986), Virology, 150:260–264.
Babiuk et al., (1975), Infect. Immun., 12:958–963.
Misra et al., (1981), J. Virol., 40:367–378.
van Drunen Littel-van den Hurk et al., (1984), Virology, 135:466–479.
Lupton et al., (1980), Am. J. Vet. Res., 41:383–390.

Primary Examiner—David B. Springer
Attorney, Agent, or Firm—Morrison & Foerster

[57] ABSTRACT

Subunit vaccines against bovine herpesvirus type 1 are provided, as well as methods of vaccination and methods of making the subunit antigen employed in the vaccines.

17 Claims, 15 Drawing Sheets

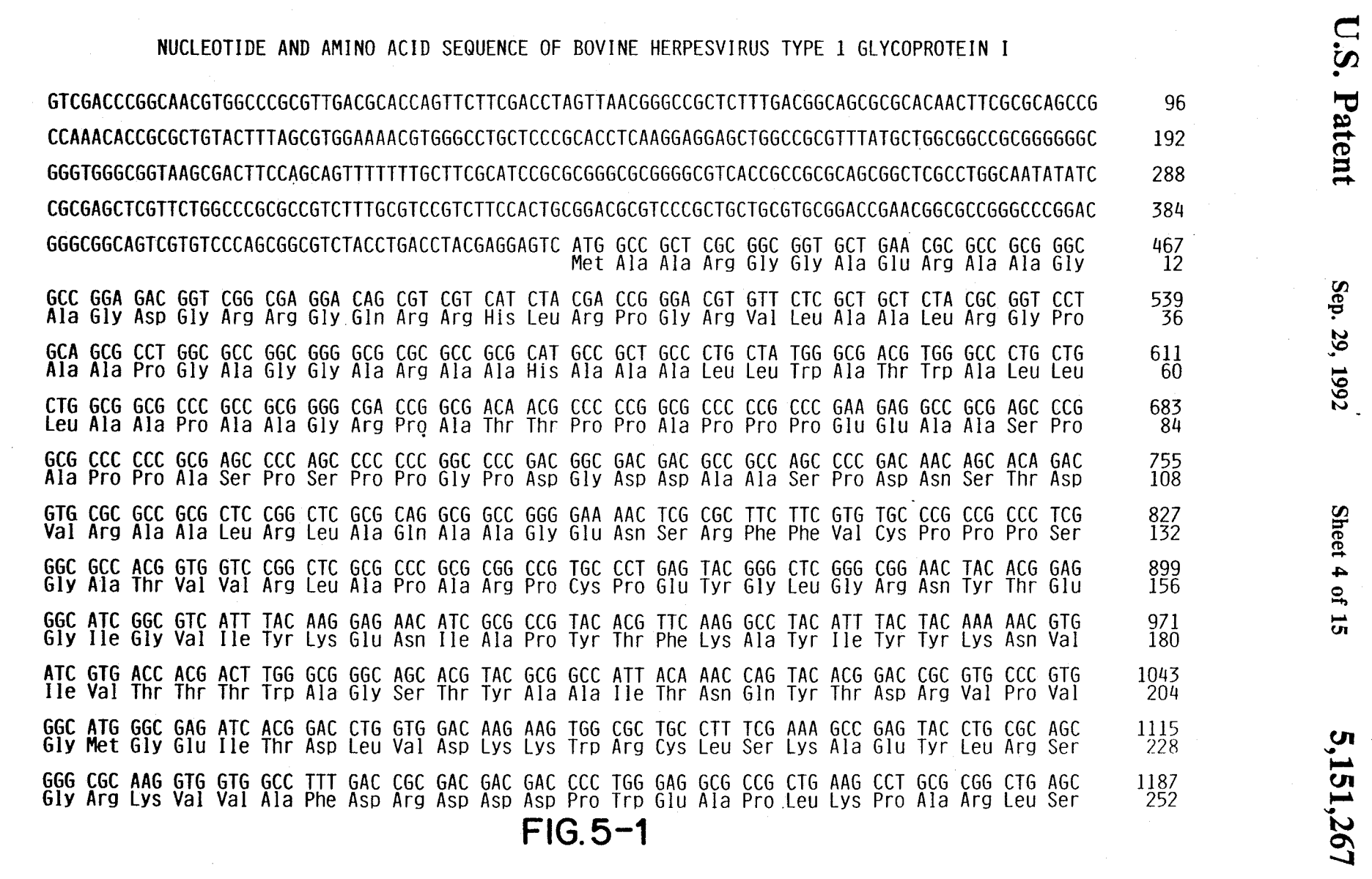

NUCLEOTIDE AND AMINO ACID SEQUENCE OF BOVINE HERPESVIRUS TYPE 1 GLYCOPROTEIN I

```
GTCGACCCGGCAACGTGGCCCGCGTTGACGCACCAGTTCTTCGACCTAGTTAACGGGCCGCTCTTTGACGGCAGCGCGCACAACTTCGCGCAGCCG   96

CCAAACACCGCGCTGTACTTTAGCGTGGAAAACGTGGGCCTGCTCCCGCACCTCAAGGAGGAGCTGGCCGCGTTTATGCTGGCGGCCGCGGGGGC  192

GGGTGGGCGGTAAGCGACTTCCAGCAGTTTTTTTGCTTCGCATCCGCGCGGGCGCGGGGCGTCACCGCCGCGCAGCGGCTCGCCTGGCAATATATC  288

CGCGAGCTCGTTCTGGCCCGCGCCGTCTTTGCGTCCGTCTTCCACTGCGGACGCGTCCCGCTGCTGCGTGCGGACCGAACGGCGCCGGGCCCGGAC  384

GGGCGGCAGTCGTGTCCCAGCGGCGTCTACCTGACCTACGAGGAGTC ATG GCC GCT CGC GGC GGT GCT GAA CGC GCC GCG GGC  467
                                                Met Ala Ala Arg Gly Gly Ala Glu Arg Ala Ala Gly   12

GCC GGA GAC GGT CGG CGA GGA CAG CGT CGT CAT CTA CGA CCG GGA CGT GTT CTC GCT GCT CTA CGC GGT CCT  539
Ala Gly Asp Gly Arg Arg Gly Gln Arg Arg His Leu Arg Pro Gly Arg Val Leu Ala Ala Leu Arg Gly Pro   36

GCA GCG CCT GGC GCC GGC GGG GCG CGC GCC GCG CAT GCC GCT GCC CTG CTA TGG GCG ACG TGG GCC CTG CTG  611
Ala Ala Pro Gly Ala Gly Gly Ala Arg Ala Ala His Ala Ala Ala Leu Leu Trp Ala Thr Trp Ala Leu Leu   60

CTG GCG GCG CCC GCC GCG GGG CGA CCG GCG ACA ACG CCC CCG GCG CCC CCG CCC GAA GAG GCC GCG AGC CCG  683
Leu Ala Ala Pro Ala Ala Gly Arg Pro Ala Thr Thr Pro Pro Ala Pro Pro Pro Glu Glu Ala Ala Ser Pro   84

GCG CCC CCC GCG AGC CCC AGC CCC CCC GGC CCC GAC GGC GAC GAC GCC GCC AGC CCC GAC AAC AGC ACA GAC  755
Ala Pro Pro Ala Ser Pro Ser Pro Pro Gly Pro Asp Gly Asp Asp Ala Ala Ser Pro Asp Asn Ser Thr Asp  108

GTG CGC GCC GCG CTC CGG CTC GCG CAG GCG GCC GGG GAA AAC TCG CGC TTC TTC GTG TGC CCG CCG CCC TCG  827
Val Arg Ala Ala Leu Arg Leu Ala Gln Ala Ala Gly Glu Asn Ser Arg Phe Phe Val Cys Pro Pro Pro Ser  132

GGC GCC ACG GTG GTC CGG CTC GCG CCC GCG CGG CCG TGC CCT GAG TAC GGG CTC GGG CGG AAC TAC ACG GAG  899
Gly Ala Thr Val Val Arg Leu Ala Pro Ala Arg Pro Cys Pro Glu Tyr Gly Leu Gly Arg Asn Tyr Thr Glu  156

GGC ATC GGC GTC ATT TAC AAG GAG AAC ATC GCG CCG TAC ACG TTC AAG GCC TAC ATT TAC TAC AAA AAC GTG  971
Gly Ile Gly Val Ile Tyr Lys Glu Asn Ile Ala Pro Tyr Thr Phe Lys Ala Tyr Ile Tyr Tyr Lys Asn Val  180

ATC GTG ACC ACG ACT TGG GCG GGC AGC ACG TAC GCG GCC ATT ACA AAC CAG TAC ACG GAC CGC GTG CCC GTG 1043
Ile Val Thr Thr Thr Trp Ala Gly Ser Thr Tyr Ala Ala Ile Thr Asn Gln Tyr Thr Asp Arg Val Pro Val  204

GGC ATG GGC GAG ATC ACG GAC CTG GTG GAC AAG AAG TGG CGC TGC CTT TCG AAA GCC GAG TAC CTG CGC AGC 1115
Gly Met Gly Glu Ile Thr Asp Leu Val Asp Lys Lys Trp Arg Cys Leu Ser Lys Ala Glu Tyr Leu Arg Ser  228

GGG CGC AAG GTG GTG GCC TTT GAC CGC GAC GAC GAC CCC TGG GAG GCG CCG CTG AAG CCT GCG CGG CTG AGC 1187
Gly Arg Lys Val Val Ala Phe Asp Arg Asp Asp Asp Pro Trp Glu Ala Pro Leu Lys Pro Ala Arg Leu Ser  252
```

FIG. 5-1

NUCLEOTIDE AND AMINO ACID SEQUENCE OF BOVINE HERPESVIRUS TYPE 1 GLYCOPROTEIN I

```
GCG CCC GGG GTG CGG GGC TGG CAC ACG GAT TAC ACG GTG GAG GGC CTG TCG GGC CTC TAC CGC   1259
Ala Pro Gly Val Arg Gly Trp His Thr Asp Tyr Thr Val Glu Gly Leu Ser Gly Leu Tyr Arg    276

ACG GGC ACC TCT GTG AAC TGC ATC ATT TAC GAA GTG GCG GAG GCG TCG TAC CCG TAC TTC GCA   1331
Thr Gly Thr Ser Val Asn Cys Ile Ile Tyr Glu Val Ala Glu Ala Ser Tyr Pro Tyr Phe Ala    300

CTC TCG ACC GGG GAC ATT ATC TAC ATG TCG CCC TTT GGG CTG CGC GCG CAC GAG CAC CGC ACC   1403
Leu Ser Thr Gly Asp Ile Ile Tyr Met Ser Pro Phe Gly Leu Arg Ala His Glu His Arg Thr    324

AGC TAC TCG CCG GAG TTC CAG CAG ATC CTG GGG TAC TAC TAC AAG CGG CGG CGG CGC CGC CTC   1475
Ser Tyr Ser Pro Glu Phe Gln Gln Ile Leu Gly Tyr Tyr Tyr Lys Arg Arg Arg Arg Arg Leu    348

AAG GAG CCG CCG TGC TCG CGG AAC TTT TTG CGT ACA CAG GTG GAC ACG GCC TGG CCC AAG CGC   1547
Lys Glu Pro Pro Cys Ser Arg Asn Phe Leu Arg Thr Gln Val Asp Thr Ala Trp Pro Lys Arg    372

AAA AAC GTG TGC TCG CTG GCC AAG TGG CGC CAC GTA CTG CGA GAC GAA ATG GCG CCC GGG AAC   1619
Lys Asn Val Cys Ser Leu Ala Lys Trp Arg His Val Leu Arg Asp Glu Met Ala Ser Gly Asn    396

CGC TTC ACG GCC CGC TCG CTC TCG ACC TTT GTG GCG GCG GAG ATG GAC CAC ACC TTC GCG AAC   1691
Arg Phe Thr Ala Arg Ser Leu Ser Thr Phe Val Ala Ala Glu Met Asp His Thr Phe Ala Asn    420

CTG AGC GAC TGC GTG ATC GAA GAG GCC TAC CTG GAG GTC CGC TAC CGC GAG GTG GCC TTC GAG   1763
Leu Ser Asp Cys Val Ile Glu Glu Ala Tyr Leu Glu Val Arg Tyr Arg Glu Val Ala Phe Glu    444

CAC GTG CTG TCG GGC AGC GGC TTG GAG CTG CTG TAC CGG GGC GGG TTT GTC GTG GCC ACG GGC   1835
His Val Leu Ser Gly Ser Gly Leu Glu Leu Leu Tyr Arg Gly Gly Phe Val Val Ala Thr Gly    468

AGC AAC GAG GCC CTG GCC AAG CTG CAG GAG TAC CTG CAG CGG CGG CGG GCG CTG AAC GGC GGC   1907
Ser Asn Glu Ala Leu Ala Lys Leu Gln Glu Tyr Leu Gln Arg Arg Arg Ala Leu Asn Gly Gly    492

GCC GCG CGG CCC CCC AAG CCC CCG CGG GCG CGG CGC CGG GGG GGC CCC TCT GCC GCC CCG GCG   1979
Ala Ala Arg Pro Pro Lys Pro Pro Arg Ala Arg Arg Arg Gly Gly Pro Ser Ala Ala Pro Ala    516

GCC GGG CCC GAC GGC GAC GCG GCG GGC GGG GCC GTG GTG ACT ACC AGC GAG TTT GCG GCG GCG   2051
Ala Gly Pro Asp Gly Asp Ala Ala Gly Gly Ala Val Val Thr Thr Ser Glu Phe Ala Ala Ala    540

CTG CAG TTC ACC TAC GAC TAC ATC CAG CAG CAC GAC GTG AAC ACC ATG TTC AGC CGC CTG TGC   2123
Leu Gln Phe Thr Tyr Asp Tyr Ile Gln Gln His Asp Val Asn Thr Met Phe Ser Arg Leu Cys    564
```

FIG. 5-2

NUCLEOTIDE AND AMINO ACID SEQUENCE OF BOVINE HERPESVIRUS TYPE 1 GLYCOPROTEIN I

```
CTG CTG CAG AAC AAG GAG CGC GCC CTG TGG GCC GAG GCG GCT AAG CTC AAC CCC AGC GCG GCG GCC AGC GCT   2195
Leu Leu Gln Asn Lys Glu Arg Ala Leu Trp Ala Glu Ala Ala Lys Leu Asn Pro Ser Ala Ala Ala Ser Ala    588

GCG CTG GAC CGC CGC GCC GCC GCG CGC ATG TTG GGG GAC GCC ATG GCC GTG ACG TAC TGC CAC GAG CTG GGC   2267
Ala Leu Asp Arg Arg Ala Ala Ala Arg Met Leu Gly Asp Ala Met Ala Val Thr Tyr Cys His Glu Leu Gly    612

GAG GGG CGC GTG TTC ATC GAG AAC TCG ATG CGC GCG CCC GGC GGC GTT TGC TAC AGC CGC CCG CCG GTC TCC   2339
Glu Gly Arg Val Phe Ile Glu Asn Ser Met Arg Ala Pro Gly Gly Val Cys Tyr Ser Arg Pro Pro Val Ser    636

TTT GCC TTC GGC AAC GAG AGC GAG CCG GTG GAG GGC CAG CTC GGC GAG GAC AAC GAG CTG CTG CCG GGC CGC   2411
Phe Ala Phe Gly Asn Glu Ser Glu Pro Val Glu Gly Gln Leu Gly Glu Asp Asn Glu Leu Leu Pro Gly Arg    660

GAG CTC GTG GAG CCC TGC ACC GCC AAC CAC AAG CGC TAC TTC CGC TTT GGC GCG GAC TAC GTG TAC TAC GAG   2483
Glu Leu Val Glu Pro Cys Thr Ala Asn His Lys Arg Tyr Phe Arg Phe Gly Ala Asp Tyr Val Tyr Tyr Glu    684

AAC TAC GCG TAC GTG CGG CGG GTC CCG CTC GCG GAG CTG GAG GTG ATC AGC ACC TTT GTG GAC CTA AAC CTC   2555
Asn Tyr Ala Tyr Val Arg Arg Val Pro Leu Ala Glu Leu Glu Val Ile Ser Thr Phe Val Asp Leu Asn Leu    708

ACG GTT CTG GAG GAC CGC GAG TTC TTG CCG CTA GAA GTG TAC ACG CGC GCC GAG CTC GCC GAC ACG GGT CTG   2627
Thr Val Leu Glu Asp Arg Glu Phe Leu Pro Leu Glu Val Tyr Thr Arg Ala Glu Leu Ala Asp Thr Gly Leu    732

CTC GAC TAC AGC GAG ATA CAG CGC CGC AAC CAG CTG CAC GAG CTC CGG TTC TAC GAC ATT GAC CGC GTG GTC   2699
Leu Asp Tyr Ser Glu Ile Gln Arg Arg Asn Gln Leu His Glu Leu Arg Phe Tyr Asp Ile Asp Arg Val Val    756

AAG ACG GAC GGC AAT ATG GCC ATC ATG CGA GGG CTC GCC AAC TTC TTT CAG GGC CTG GGC GCC GTC GGG CAG   2771
Lys Thr Asp Gly Asn Met Ala Ile Met Arg Gly Leu Ala Asn Phe Phe Gln Gly Leu Gly Ala Val Gly Gln    780

GCG GTG GGC ACG GTG GTG CTG GGC GCC GCG GGT GCC GCG CTC TCG ACC GTG TCG GGC ATC GCC TCG TTT ATT   2843
Ala Val Gly Thr Val Val Leu Gly Ala Ala Gly Ala Ala Leu Ser Thr Val Ser Gly Ile Ala Ser Phe Ile    804

GCG AAC CCG TTC GGC GCG CTG GCC ACG GGG CTG CTG GTG CTC GCC GGG CTG GTG GCC GCT TTC CTG GCG TAC   2915
Ala Asn Pro Phe Gly Ala Leu Ala Thr Gly Leu Leu Val Leu Ala Gly Leu Val Ala Ala Phe Leu Ala Tyr    828

CGG TAC ATT TCC CGC CTC CGC AGC AAC CCC ATG AAG GCG CTG TAC CCG ATC ACC ACG CGC GCG CTC AAG GAC   2987
Arg Tyr Ile Ser Arg Leu Arg Ser Asn Pro Met Lys Ala Leu Tyr Pro Ile Thr Thr Arg Ala Leu Lys Asp    852

GAC GCC CGG GGC GCA ACC GCC CCG GGC GAG GAA GAG GAG GAG TTT GAC GCG GCC AAA CTG GAG CAG GCC CGC   3059
Asp Ala Arg Gly Ala Thr Ala Pro Gly Glu Glu Glu Glu Glu Phe Asp Ala Ala Lys Leu Glu Gln Ala Arg    876
```

FIG.5-3

NUCLEOTIDE AND AMINO ACID SEQUENCE OF BOVINE HERPESVIRUS TYPE 1 GLYCOPROTEIN I

```
GAG ATG ATC AAG TAT ATG TCG CTC GTG TCA GCG GTC GAG CGG CAA GAG CAC AAG GCG AAA AAG AGC AAC AAG     3131
Glu Met Ile Lys Tyr Met Ser Leu Val Ser Ala Val Glu Arg Gln Glu His Lys Ala Lys Lys Ser Asn Lys      900

GGC GGC CCG CTG CTG GCG ACC CGG CTG ACG CAG CTC GCG CTT CGG CGG CGA GCG CCG CCG GAG TAC CAG CAG     3203
Gly Gly Pro Leu Leu Ala Thr Arg Leu Thr Gln Leu Ala Leu Arg Arg Arg Ala Pro Pro Glu Tyr Gln Gln      924

CTT CCG ATG GCC GAC GTC GGG GGG GCA TGA GGCCTATGTATGGGCAGTTCGGGTGCCAATAATAAATTTTGCGCGAATCTTATTT     3288
Leu Pro Met Ala Asp Val Gly Gly Ala ---                                                              933

AAGTGCACACCGTGTTATTTGCGGCTGTTTGTTTTTCCTGGAGGCGGGACGCTGCGCGCGAGCTCGGCCGGATTAGGGTTCGGCGCCACCCGGG      3382
```

FIG.5-4

NUCLEOTIDE AND AMINO ACID SEQUENCE OF BOVINE HERPESVIRUS TYPE 1 GLYCOPROTEIN III

```
CGGCCTGCAGCCGGCGGTGTGCTCAATCCCGGACCGAAGCACAAAACGGACGCCCTTAAAATGTAGCCCGGCCGGTCGCGGCCATCTT                96
GGATCCACCCGGCGACCCGGAGACCGCAGCCCGGAGACCTCGCCGCGTCCGCC ATG GGC CCG CTG GGG GAG GCG GAA GCG TGG           183
                                                       Met Gly Pro Leu Gly Glu Ala Glu Ala Trp           8

CTG ATC GCA GCT ATT TTC GCC TGG GCG CTC TCT GCG CGG GGG CTC GCC GAG GCG GAA GCC TCT                    255
Leu Ile Ala Ala Ile Phe Ala Trp Ala Leu Ser Ala Arg Gly Leu Ala Glu Ala Glu Ala Ser                     32

CCC TCG CCT CCG CCC TCC CCG TGC ACC GAA AGC TCC GCT GGT GCA ACC GGC GCA ACG CCC CCC                    327
Pro Ser Pro Pro Pro Ser Pro Cys Thr Glu Ser Ser Ala Gly Ala Thr Gly Ala Thr Pro Pro                     56

ACG CCC AAC AGC CCC GAC GCT ACG GAG GAC AGC CCC GTT ACC ACG CCC GTG GGG ACG CCG GAG                    399
Thr Pro Asn Ser Pro Asp Ala Thr Glu Asp Ser Pro Val Thr Thr Pro Val Gly Thr Pro Glu                     80

CCG CCG TCC GTG TCC GAG CAC GAC CCG CCC GAT GGC CGA CCT GGG GGG GAC GGG                                471
Pro Pro Ser Val Ser Glu His Asp Pro Pro Asp Gly Arg Pro Gly Gly Asp Gly                                104

CGA CCC GGC GGT GCT AAC GGC AGC GCA CGG GAG CGC CCC CCT CGC CCG CCG CGG                                543
Arg Pro Gly Gly Ala Asn Gly Ser Ala Arg Glu Arg Pro Pro Arg Pro Pro Arg                                128

CCG AGC AAA GCC CCG AAG GAG ATG TGC CTC GAG GCG GTG CTG GCC TCG TAC GCC                                615
Pro Ser Lys Ala Pro Lys Glu Met Cys Leu Glu Ala Val Leu Ala Ser Tyr Ala                                152

GAG CCG TAC GTG CAC TGC ACT GGC GCA CGC CGC GAG CTG TGG TTT CAG CCC                                    687
Glu Pro Tyr Val His Cys Thr Gly Ala Arg Arg Glu Leu Trp Phe Gln Pro                                    176

CGC GTG GGC AGG TTC CGC ACG TCC CGC GTG GCA GAC GGC CTG CCG CGG GCC CCG                                759
Arg Val Gly Arg Phe Arg Thr Ser Arg Val Ala Asp Gly Leu Pro Arg Ala Pro                                200

GTG CTG TTC GTA GCC CAG GGC ATC GCG TAC CGT GAG CTG GAC TAT ATT TCC                                    831
Val Leu Phe Val Ala Gln Gly Ile Ala Tyr Arg Glu Leu Asp Tyr Ile Ser                                    224

CCT TCG GAC GCC CCC AAC CCC CGC CGT GTC ACC TCC AGC GCC GAG GTG TAC                                    903
Pro Ser Asp Ala Pro Asn Pro Arg Arg Val Thr Ser Leu Ala Ala Glu Val Tyr                                248

ACT TGG CGC GAC ATG GGG TCA CAG AAG CGC GTC GTG ACG CAC CCC GCT                                        975
Thr Trp Arg Asp Met Gly Ser Gln Lys Arg Val Val Thr His ARg Pro Ala                                    272
```

FIG.6-1

NUCLEOTIDE AND AMINO ACID SEQUENCE OF BOVINE HERPESVIRUS TYPE 1 GLYCOPROTEIN III

GTT TCC GTC GAA CCC CAG CCA GCG CTA GAA GGC GCC GGC TAC GCG GCC GTG TGC CGC GCC GCC GAG TAC TAC 1047
Val Ser Val Glu Pro Gln Pro Ala Leu Glu Gly Ala Gly Tyr Ala Ala Val Cys Arg Ala Ala Glu Tyr Tyr 296

CCG CCG CGC TCC ACG CGC CTG CAC TGG TTC CGC AAC GGC TAC CCC GTG GAG GCT CGG CAC GCG CGC GAC GTC 1119
Pro Pro Arg Ser Thr Arg Leu His Trp Phe Arg Asn Gly Tyr Pro Val Glu Ala Arg His Ala Arg Asp Val 320

TTT ACG GTC GAC GAC TCC GGG CTC TTT TCG CGC ACG TCC GTC CTT ACG CTC GAG GAC GCG ACG CCA ACC GCC 1191
Phe Thr Val Asp Asp Ser Gly Leu Phe Ser Arg Thr Ser Val Leu Thr Leu Glu Asp Ala Thr Pro Thr Ala 344

CAC CCG CCC AAC CTG CGC TGC GAC GTC TCC TGG TTC CAG AGC GCT AAC ATG GAG CGC CGC TTT TAC GCG GCT 1263
His Pro Pro Asn Leu Arg Cys Asp Val Ser Trp Phe Gln Ser Ala Asn Met Glu ARg Arg Phe Tyr Ala Ala 368

GGC ACG CCG GCC GTT TAC CGC CCG CCC GAG CTG CGC GTG TAC TTC GAG GGC GGC GAG GCC GTC TGC GAG GCG 1335
Gly Thr Pro Ala Val Tyr Arg Pro Pro Glu Leu Arg Val Tyr Phe Glu Gly Gly Glu Ala Val Cys Glu Ala 392

CGC TGC GTC CCC GAG GGG CGC GTC TCC CTG CGC TGG ACG GTG CGC GAC GGC ATC GCC CCG TCG CGC ACT GAG 1407
Arg Cys Val Pro Glu Gly ARg Val Ser Leu Arg Trp Thr Val Arg Asp Gly Ile Ala Pro Ser Arg Thr Glu 416

CAG ACC GGC GTC TGC GCC GAG CGG CCC GGG CTG GTA AAC CTG CGC GGC GTG CGC CTG CTT TCT ACA ACC GAC 1479
Gln Thr Gly Val Cys Ala Glu Arg Pro Gly Leu Val Asn Leu Arg Gly Val ARg Leu Leu Ser Thr Thr Asp 440

GGG CCC GTC GAC TAC ACC TGC ACC GCC ACT GGC TAC CCG GCA CCG CTG CCC GAG TTC TCC GCG ACC GCC ACG 1551
Tly Pro Val Asp Tyr Thr Cys Thr Ala Thr Gly Tyr Pro Ala Pro Leu Pro Glu Phe Ser Ala Thr Ala Thr 464

TAC GAC GCC TCG CCC GGC CTA ATC GGA AGC CCC GTC CTC GTC AGC GTC GTG GCC GTC GCC TGC GGT CTC GGC 1623
Tyr Asp Ala Ser Pro Gly Leu Ile Gly Ser Pro Val Leu Val Ser Val Val Ala Val Ala Cys Gly Leu Gly 488

GCC GTG GGG CTC CTG CTG GTG GCG GCC TCG TGC CTG CGG CGC AAG GCC CGG GTA ATC CAA CCC GGT CTT ACT 1695
Ala Val Gly Leu Leu Leu Val Ala Ala Ser Cys Leu Arg Arg Lys Ala Arg Val Ile Gln Pro Gly Leu Thr 512

CGC GCT CGC GCC CTC GGC TCC GCG CCC TAG ACGACCGGCACGGCCTGGAGGCGCTGGCGGCTGCCGGTGCCGCTCACACCGCGCG 1780
Arg Ala ARg Ala Leu Gly Ser Ala Pro --- 521

CCACAACCGCGACGTGTGGCAGCGCTTTTCCCGCGTCTGCGAGGCCGGC

FIG.6-2

NUCLEOTIDE AND AMINO ACID SEQUENCE OF BOVINE HERPESVIRUS TYPE GLYCOPROTEIN IV

```
GGGCCGCAGCCCGGCTGGGTATATATCCCGACGGGCGACTAGAGATACACTCGCCCCGGCCGGCTGCTGCGAGCGGGCGAAC ATG CAA GGG          93
                                                                                  Met Gln Gly           3

CCG ACA TTG GCC GTG CTG GGC GCC GTT GCG GTG AGC TTG CCT ACA CCC GCG CCG CGG GTG ACG          165
Pro Thr Leu Ala Val Leu Gly Ala Val Ala Val Ser Leu Pro Thr Pro Ala Pro Arg Val Thr           27

GTA TAC GTC GAC CCG CCG TAC GCG CCG ATG CCG CGA TAC AAC TAC ACT GAA CGC TGG CAC ACT AAC GGG CCC          237
Val Tyr Val Asp Pro Pro Tyr Ala Pro Met Pro Arg Tyr Asn Tyr Thr Glu Arg Trp His Thr Gly Pro              51

ATA CCG TCG CCC TTC GCA GAC GGC GAG CAG GTG GGG CGC TAC GTC GAG CCC GTC GCG AGC GCG TGC          309
Ile Pro Ser Pro Phe Ala Asp Gly Glu Gln Val Gly Arg Tyr Val Glu Pro Val Ala Ser Ala Cys          75

GAC ATG CTG GCG ATC GCA GAC CCG TAC AAG ATC GAG ACG CGG ACG CTG TGG CAC CGG TAC ATG CGC          381
Asp Met Leu Ala Ile Ala Asp Pro Tyr Lys Ile Glu Thr ARg Thr Leu Trp His Arg Tyr Met Ala Arg      99

GCG TAC AAC GCC ACG GTC ATA ATC TTT GGG TAC TGC CGC CCG CTG TAC CTG TAC TAT GAG TAC          453
Ala Tyr Asn Ala Thr Val Ile Ile Phe Gly Tyr Cys Arg Pro Leu Tyr Leu Tyr Tyr Glu Tyr          123

ACC GAG TGC GAG CCC AGG AAG CAC TTT GGG TAC TGC CGC ACA CCC CCG TTT TGG GAC AGC TTC CTG          525
Thr Glu Cys Glu Pro ARg Lys His Phe Gly Tyr Cys Arg Thr Pro Pro Phe Trp Asp Ser Phe Leu         147

GCG GGC TTC GCC TAC CCG ACG GAC GAC ATG ATG CTG GGA CTG CTG ATG ATT ATC ATG GCG GCG CCC GCC CTC GTC GAG GGC          597
Ala Gly Phe Ala Tyr Pro Thr Asp Asp Met Met Leu Gly Leu Leu Met Ile Ile Met Ala Ala Pro Ala Leu Val Glu Gly         171

CAG TAC CGA CGC GCG ATC TAC GCG GTC GAC TTC ACA TAT ACC TTT CCG CCG CTG CCG          669
Gln Tyr Arg Arg Ala Ile Tyr Ala Val Asp Phe Met Thr Thr Thr Phe Pro Pro Leu Pro          195

GAC TGC TGG TCG AAA CTC GGC GCG GCG GCG TAC TAC GGG GGC TGC TTC GCC CGG GAT TAC          741
Asp Cys Trp Ser Lys Leu Gly Ala Ala Ala Tyr Tyr Gly Gly Cys Phe Ala Arg Asp Tyr          219

GAG CAA AAG GTT CTG CGC ACG TAT CTC CAG CAG TTT CCG CCG GAG GAG CCG GCA CAC AAG GCC ATA GTC          813
Glu Gln Lys Val Leu Arg Thr Tyr Leu Gln Gln Phe Pro Pro Glu Glu Pro Ala His Lys Ala Ile Val         243

GAC TAC TGG ATG CGC CGC CAC GGC GTT CCG CCA TAT TTT GAG GAG TCG AAG GGC TAC GAG CCG          885
Asp Tyr Trp Met ARg Arg His Gly Val Pro Pro Tyr Phe Glu Glu Ser Lys Gly Tyr Glu Pro          267

CCT GCC GCC GAT GGG GGT TCC CCC GCG GGC GAC GAC GAG GCC CGC GAT GAA GGG GAG ACC GAG          957
Pro Ala Ala Asp Gly Gly Ser Pro Ala Gly Asp Asp Glu Ala Arg Asp Glu Gly Glu Thr Glu          291
```

FIG.7-1

NUCLEOTIDE AND AMINO ACID SEQUENCE OF BOVINE HERPESVIRUS TYPE GLYCOPROTEIN IV

```
GAC GGG GCA GCC GGG CGG GAG GGC AAC GGC CCC CCA GGA CCC GAA GGC GAC GGC GAG AGT CAG ACC CCC   1029
Asp Gly Ala Ala Gly ARg Glu Gly Asn Gly Pro Pro Gly Pro Glu Gly Asp Gly Glu Ser Gln Thr Pro    315

GAA GCC AAC GGA GCC GAG GGC GAG GGC CCG AAA CCC GGC CCC AGC GAC CCC GAC GCC CGC GAA GGC TGG   1101
Glu Ala Asn Gly Ala Glu Gly Ala Gly Pro Lys Pro Gly Pro Ser Asp Pro Asp Ala ARg Pro Gly Trp   339

CCG AGC GAA GCC ATC ACG CAC CCC GGC GCT ACG CCC GAC CCC GCC GTG CCG GTC   1173
Pro Ser Leu Glu Ala Ile Thr His Pro Gly Ala Thr Pro Ala Pro Asp Ala Val Pro Val                363

AGC GTC GGG ATC GGC ATT GCG GCT GCG GCG ATC GCG GCG TGC GTG GCC GCC GCC GCC GCC GCG TAC TTC GTC   1245
Ser Val Gly Ile Gly Ile ala Ala Ala Ala Ala Ile Ala Cys Val Ala Ala Ala Ala Ala Gly Ala Tyr Phe Val   387

TAT ACG CGC CGG CGC GGT GCG GGA CCG CTG CCC AGA AAG CCA AAA AAG CTG CCG GCC TTT GGC AAC GTC AAC   1317
Tyr Thr Arg Arg Arg Gly Ala Gly Pro Leu Pro Arg Lys Pro Lys Lys Leu Pro Ala Phe Gly Asn Val Asn   411

TAC AGC GCG CTG CCC GGG TGA GCGGGCCTAGGCCCCTCCCCCGACCGCCCCCTTTGCTCCTAGCCCCGGCTCCTGCCGAGCCGGCGGGG   1405
Tyr Ser Ala Leu Pro Gly ---                                                                         417
```

FIG.7-2

BOVINE HERPESVIRUS TYPE 1 POLYPEPTIDES AND VACCINES

TECHNICAL FIELD

The present invention is directed to subunit vaccines for use in cattle to protect against bovine herpesvirus type 1 infection. The present invention is also directed to materials and methods useful in the production of such subunit vaccines, as well as methods of using the subunit vaccines.

BACKGROUND

Bovine herpesvirus type 1 (BHV-1) is an economically significant pathogen of cattle. BHV-1, which is also known as infectious bovine rhinotracheitis virus, causes severe respiratory infections, conjunctivitis, vulvovaginitis, abortions, encephalitis, and generalized systemic infections. If an animal recovers from a primary infection, the virus remains in the host in a latent state. Reactivation of the virus can be provoked by certain endogenous or exogenous physical modifications in the animal, or experimentally by treatment of the animal with glucocorticoids like dexamethasone.

In an effort to control BHV-1 infections, killed virus and attenuated live-virus vaccines have been developed. While these vaccines appear to induce some level of protection in cattle, the level of immunity is well below the level necessary to afford complete or near-complete protection. For example, the vaccines do not always prevent the establishment of a latent infection by a virulent field strain of BHV-1. Furthermore, the safety of the live-virus vaccines has been questioned. It has been shown recently that two live BHV-1 vaccine strains can be reactivated by the use of dexamethasone, indicating that at least some BHV-1 vaccines can themselves establish a latent infection. See, e.g., Gerber et al. (1978) Am. J. Vet. Res. 39:753–760; Jericho et al. (1983) Can. J. Com. Med. 47:133–139; Pastoret et al. (1980) Infect. Immun. 29:483–488. Despite the recognized need for more efficacious and safer BHV-1 vaccines, no such vaccines have been developed or tested prior to the present invention.

There have been various in vitro studies published regarding the immunology of BHV-1. None of these studies, however, are predictive with regard to the efficacy of any vaccine. For example, Babiuk et al. (1975) Infect. Immun. 12:958–963, is directed to in vitro studies regarding the interaction between BHV-1 and susceptible host cells and the susceptibility of infected host cells to antibody-complement cell lysis. Misra et al. (1981) J. Virol. 40:367–378, reports on the partial characterization of a number of BHV-1 polypeptides and their immunoprecipitation with antiserum. van Drunen Littel-van den Hurk et al. (1984) Virology 135:466–479 and van Drunen Littel-van den Hurk et al. (1985) Virology 144:216–227 are directed to monoclonal antibodies developed against BHV-1 glycoproteins, and the ability of the monoclonal antibodies to neutralize virus and participate in antibody-dependent complement-mediated lysis in vitro. See also Collins et al. (1984) J. Virol. 52:403–409; Okazaki et al. (1986) Virology 150 260–264. van Drunen Littel-van den Hurk et al. (1985) Virology 144:204–215 is directed to the purification of BHV-1 glycoproteins by immunoadsorbent chromatography and the production of antiserum in rabbits. van Drunen Littel-van den Hurk et al. (1986) J. Clin. Microbiol. 23:274–282 is directed to in vitro immunoreactivity of purified BHV-1 glycoproteins and bovine antiserum. Okazaki et al. (1987) Arch. Virol. 92:17–26 is directed to in vitro studies of the reactivities of monoclonal antibodies against BHV-1 glycoproteins with infected cells.

With the exception of purification by electrophoresis or immunoadsorbent chromatography (see references cited above), virus- or cell-free BHV-1 antigens have not been produced. In particular, prior to the present invention, recombinant BHV-1 polypeptides were not available. It was unknown, therefore, whether recombinant polypeptides would be immunologically authentic. Mayfield et al. (1983) J. Virol. 47:259–264 discloses the cloning of a BHV-1 strain and a restriction map. Pachl et al. (1987) J. Virol. 61:315–325, while not directed to BHV-1, discloses the recombinant expression of a glycoprotein from the human pathogen herpes simplex virus type 1. There was no demonstration, however, that the recombinant polypeptide from the human virus is, in fact, protective in a human host. See also PCT Pub. No. W088/02634; U.S. Pat. Nos. 4,661,349; 4,642,333.

Babiuk et al. (1987) Virology 159:57–66 is a partial disclosure of the work leading to the present invention, published after the present invention was made.

SUMMARY OF THE INVENTION

It has been discovered that subunit vaccines based on selected BHV-1 glycoproteins will fully protect cattle from disease. Surprising, these subunit vaccines are substantially more protective than prior art killed virus and attenuated live-virus vaccines. The subunit vaccines of the present invention also eliminate the risk of infection from the live-virus vaccines. Furthermore, it has been discovered that recombinant BHV-1 polypeptides maintain the proper epitopes necessary to fully protect immunized animals from disease. Both non-glycosylated polypeptides, and polypeptides glycosylated by heterologous host organisms effectively elicit antibodies that neutralize virus infectivity and induce complement-mediated cell lysis. Based on these discoveries, the present invention can take several embodiments.

In one embodiment, the present invention is directed to a method of protecting a bovine host from BHV-1 infection comprising: (a) providing a vaccine composition comprising (i) a pharmaceutically acceptable vehicle, and (ii) at least one subunit antigen comprising a polypeptide neutralizing epitope of a BHV-1 glycoprotein selected from the group consisting of gI, gIII and gIV; and (b) administering an effective amount of said vaccine composition to said bovine host whereby neutralizing anti-BHV-1 antibodies are elicited in said bovine host.

In another embodiment, the present invention is directed to a vaccine composition for BHV-1 comprising: (a) a pharmaceutically acceptable vehicle; (b) a subunit antigen comprising polypeptide neutralizing epitope(s) of BHV-1 glycoprotein(s) selected from the group consisting of gIV, gI/gIII, gI/gIV, gIII/gIV, and gI/gIII/gIV.

In yet another embodiment of the present invention, a vaccine composition for BHV-1 is provided comprising: (a) a pharmaceutically acceptable vehicle; and (b) a subunit antigen comprising a recombinant polypeptide containing neutralizing epitope(s) of BHV-1 glycoprotein(s) selected from the group consisting of gI, gIII, gIV.

A further embodiment of the present invention is directed to a DNA construct comprising an expression cassette comprised of: (a) a DNA coding sequence for a polypeptide containing neutralizing epitope(s) of at least one BHV-1 glycoprotein selected from the group consisting of gI, gIII, and gIV; and (b) control sequences that are operably linked to said coding sequence whereby said coding sequence can be transcribed and translated in a host cell, at least one of said control sequences being heterologous to said coding sequence.

The present invention is also directed to host cells transformed with this expression cassette, as well as methods of making recombinant BHV-1 subunit antigens using such transformed host cells.

These and other embodiments of the present invention will readily be apparent to those of skill in the art from the following disclosure.

BRIEF DESCRIPTION OF THE FIGURES

FIG. 5 shows the nucleotide sequence and deduced amino acid sequence from a viral clone of the gI gene. This gene encodes the gIa/gIb/gIc complex. The gIa precursor is cleaved into two peptides, gIb and gIc, which are linked by disulfide bonds to produce mature gIa. The gIb peptide is 438 amino acids long and encoded at the N-terminus of the gI gene. The gIc peptide is 428 amino acids long and encoded at the C-terminus of the gI gene. Right-angle arrows show the start of the gIb and gIc peptides, and putative transmembrane sequences are underlined. See Example II.B.1.

FIG. 6 is the nucleotide sequence and deduced amino acid sequence from a viral clone of gIII. The gene encodes a 521 amino acid peptide. Putative transmembrane sequences are underlined. See Example II.B.1.

FIG. 7 is the nucleotide sequence and deduced amino acid sequence from a viral clone of gIV. The gene encodes a peptide 417 amino acids long. The right-angle arrow marks the position of the mature gIV sequence. Putative transmembrane sequences are underlined.

DETAILED DESCRIPTION

Figure 1:
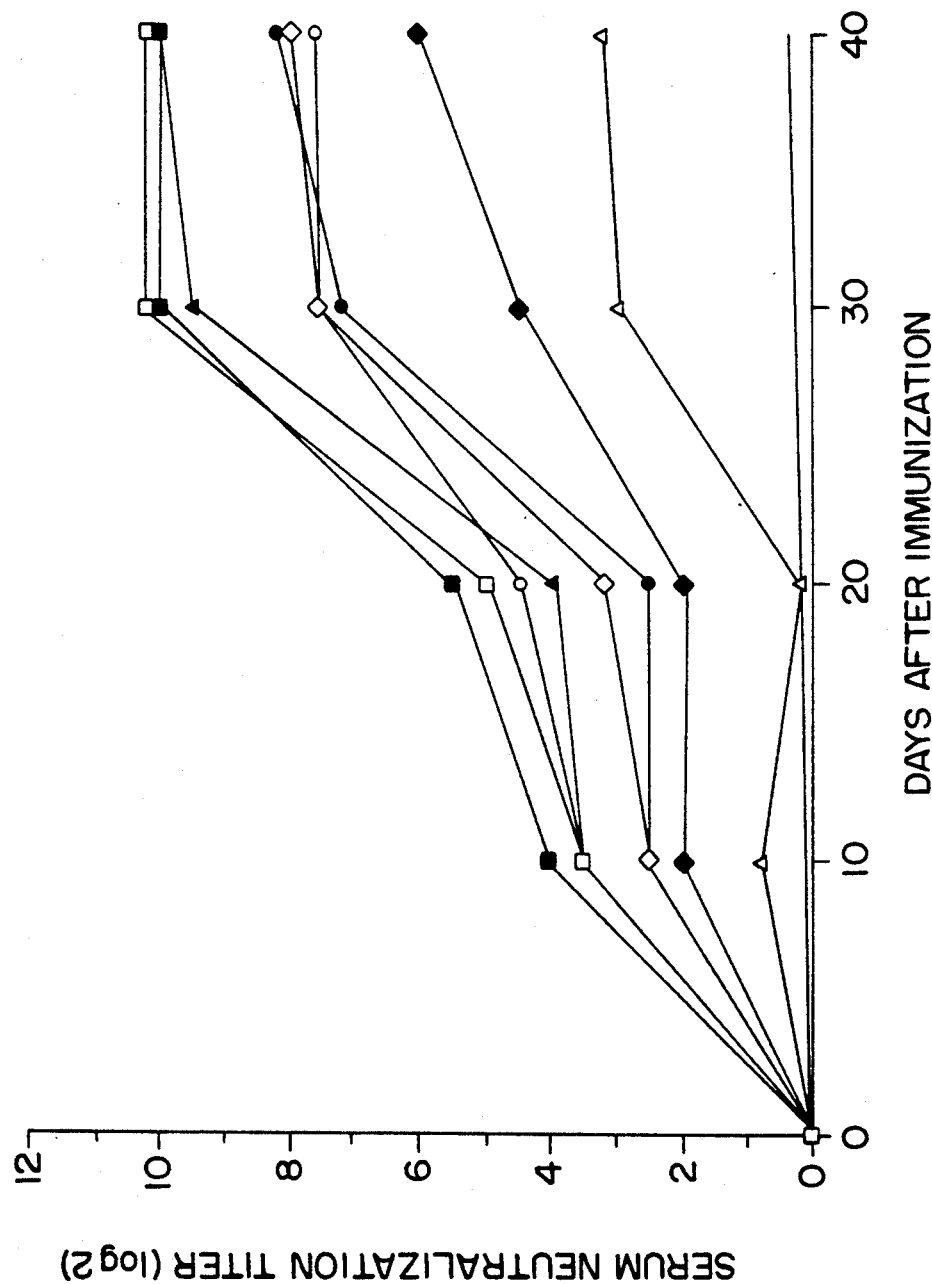
FIG. 1 shows the serum neutralizing antibody responses of animals immunized with BHV-1 glycoproteins. Animals were immunized with various glycoproteins and boosted three weeks later. Titers were determined by a 50% end point using 100 PFU of BHV-1 virus. The various glycoproteins are indicated as follows: gI (solid diamond), gIII (solid circle), gIV (solid square), gI/gIII (open diamond), gI/gIV (open square), gIII/gIV (solid triangle), gI/gIII/gIV (open circle), commercial killed vaccine (open triangle), and placebo (-). See Example I.B.1.

The practice of the present invention will employ, unless otherwise indicated, conventional virology, microbiology, molecular biology and recombinant DNA techniques within the skill of the art. Such techniques are explained fully in the literature. See, e.g., Maniatis et al., *Molecular Cloning: A Laboratory Manual* (1982); *DNA Cloning: A Practical Approach*, vol. I & II (D. Glover, ed.); *Oligonucleotide Synthesis* (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); Perbal, *A Practical Guide to Molecular Cloning* (1984).

The following terminology will be used in accordance with the definitions set out below in describing the present invention.

A "replicon" is any genetic element (e.g., plasmid, chromosome, virus) that functions as an autonomous unit of DNA replication in vivo; i.e., capable of replication under its own control.

A "vector" is a replicon, such as a plasmid, phage, or cosmid, to which another DNA segment may be attached so as to bring about the replication of the attached segment.

A "double-stranded DNA molecule" refers to the polymeric form of deoxyribonucleotides (adenine, guanine, thymine, or cytosine) in its normal, double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having the sequence homologous to the mRNA).

A DNA "coding sequence" is a DNA sequence which is transcribed and translated into a polypeptide in vivo when placed under the control of appropriate regulatory sequences. The boundaries of the coding sequence are determined by a start codon at the 5' (amino) terminus and PATENT a translation stop codon at the 3' (carboxy) terminus. A coding sequence can include, but is not limited to, procaryotic sequences, cDNA from eucaryotic mRNA, genomic DNA sequences from eucaryotic (e.g., mammalian) DNA, and even synthetic DNA sequences. A polyadenylation signal and transcription termination sequence will usually be located 3' to the coding sequence.

A "promoter sequence" is a DNA regulatory region capable of binding RNA polymerase in a cell and initiating transcription of a downstream (3' direction) coding sequence. For purposes of defining the present invention, the promoter sequence is bound at the 3' terminus by the translation start codon (ATG) of a coding sequence and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eucaryotic promoters will often, but now always, contain "TATA" boxes and "CAT" boxes. Procaryotic promoters contain Shine-Dalgarno sequences in addition to the -10 and -35 consensus sequences.

DNA "control sequences" refers collectively to promoter sequences, ribosome binding sites, polyadenylation signals, transcription termination sequences, upstream regulatory domains, enhancers, and the like, which collectively provide for the transcription and translation of a coding sequence in a host cell.

A coding sequence is "operably linked to" or "under the control of" control sequences in a cell when RNA polymerase will bind the promoter sequence and transcribe the coding sequence into mRNA, which is then translated into the polypeptide encoded by the coding sequence.

A "host cell" is a cell which has been transformed, or is capable of transformation, by an exogenous DNA sequence.

A cell has been "transformed" by exogenous DNA when such exogenous DNA has been introduced inside the cell membrane. Exogenous DNA may or may not be integrated (covalently linked) to chromosomal DNA making up the genome of the cell. In procaryotes and yests, for example, the exogenous DNA may be maintained on an episomal element, such as a plasmid. With respect to eucaryotic cells, a stably transformed cell is one in which the exogenous DNA has become integrated into the chromosome so that it is inherited by daughter cells through chromosome replication. This stability is demonstrated by the ability of the eucaryotic cell to establish cell lines or clones comprised of a population of daughter cells containing the exogenous DNA.

A "clone" is a population of cells derived from a single cell or common ancestor by mitosis. A "cell line" is a clone of a primary cell that is capable of stable growth in vitro for many generations.

Two DNA or polypeptide sequences are "substantially homologous" when at least about 85% (preferably at least about 90%, and most preferably at least about 95%) of the nucleotides or amino acids match over a defined length of the molecule. DNA sequences that are substantially homologous can be identified in a Southern hybridization experiment under, for example, stringent conditions, as defined for that particular system. Defining appropriate hybridization conditions is within the skill of the art. See, e.g., Maniatis et al., supra; *DNA Cloning,* vols I & II, supra; *Nucleic Acid Hybridization,* supra.

A "heterologous" region of a DNA construct is an identifiable segment of DNA within or attached to another DNA molecule that is not found in association with the other molecule in nature. Thus, when the heterologous region encodes a viral gene, the gene will usually be flanked by DNA that does not flank the viral gene in the genome of the source virus or virus-infected cells. Another example of the heterologous coding sequence is a construct where the coding sequence itself is not found in nature (e.g., synthetic sequences having codons different from the native gene). Allelic variation or naturally occurring mutational events do not give rise to a heterologous region of DNA, as used herein.

A composition containing molecule A is "substantially free of" molecule B when at least about 75% by weight of the total of A + B in the composition is molecule A. Preferably, molecule A comprises at least about 90% by weight of the total of A + B in the composition, more preferably at least about 99% by weight.

"Bovine host" refers to cattle of any breed for which it may be desirable to immunize against BHV-1 infection, whether or not the bovine host is already infected or latently infected by BHV-1.

The term "protein" or "glycoprotein" is used herein to designate a naturally occurring polypeptide or glycosylated polypeptide, respectively. The term "polypeptide" is used in its broadest sense, i.e., any polymer of amino acids (dipeptide or greater) linked through peptide bonds. Thus, the term "polypeptide" includes proteins, oligopeptides, protein fragments, analogs, muteins, fusion proteins and the like.

"Native" proteins or polypeptides refer to proteins or polypeptides recovered from BHV-1 virus or BHV-1-infected cells. Thus, the term "native BHV-1 polypeptide" would include naturally occurring BHV-1 proteins and fragments thereof. "Non-native" polypeptides refer to polypeptides that have been produced by recombinant DNA methods or by direct synthesis. "Recombinant" polypeptides refer to polypeptides produced by recombinant DNA techniques; i.e., produced from cells transformed by an exogenous DNA construct encoding the desired polypeptide.

Bovine herpesvirus type 1, or BHV-1, is a well-known and well-characterized virus, of which many strains are known. See, e.g., Gibbs et al. (1977) Vet. Bull. (London) 47:317-343. BHV-1, also known as infectious bovine rhinotracheitis virus, is similar in structure to other herpesviruses, and possesses a linear double-stranded DNA genome of approximately 140 kilobase pairs. BHV-1 can remain latent in infected animals, probably in trigeminal or sacral ganglia, and, as discussed above, can be reactivated with relative ease.

The BHV-1 genome specifies more than 25 structural polypeptides, of which about 11 are believed to be glycosylated. Of particular interest to the present invention are the glycoproteins gI (previously referred to as GVP 6/11a/16), gIII (previously referred to as GVP 9 or its dimer, GVP 3), and gIV (previously referred to as GVP 11b). Glycoprotein gI is a complex of three glycoproteins with apparent molecular weights of approximately 130 k (gIa), 74 k (gIb), and 55 k (gIc). gIa is the precursor of gIb and gIc. Glycoprotein gIII has an apparent molecular weight of about 91 k and also occurs as a dimer with an approximate apparent molecular weight of 180 k. Glycoprotein gIV has an apparent molecular weight of approximately 71 k, and also occurs as an approximate 140 k dimer.

Figure 4:
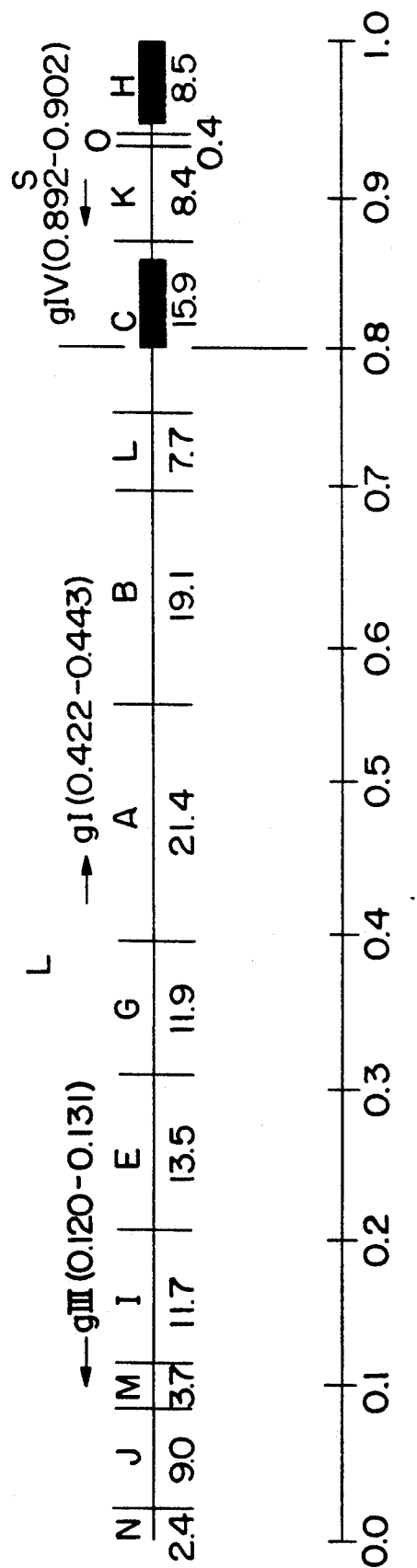
FIG. 4 shows the genomic location of BHV-1's major glycoprotein genes. The position and direction of transcription for the gIII, gI and gIV genes are shown by the arrows above the genomic map. HindIII sites are marked by vertical lines, and the size in kilobase pairs is shown below the genomic map. The scale below the map measures genomic equivalents. Numbers next to gene designations show their position in genomic equivalents. See Example II.B.1.

The BHV-1 gene for gI maps between 0.422 and 0.443 genome equivalents (FIG. 4) in the HindIII A fragment described by Mayfield et al. (1983), supra. The gIII gene maps between 0.120 and 0.131 genome equivalents (FIG. 4) in the HindIII I fragment. Id. The gIV gene maps between 0.892 and 0.902 genome equivalents in the HindIII K fragment. The nucleotide sequences of the gI, gIII, and gIV genes are shown in FIGS. 5, 6, and 7, respectively.

A key aspect of the present invention is the provision of a subunit antigen useful in the production of BHV-1 vaccines. A subunit antigen is an antigen entity separate and discrete from a whole virus (live or killed) or virus-infected cell. The subunit antigens of the present invention are polypeptides from at least one of the BHV-1 glycoproteins gI, gIII, or gIV. In general, the polypeptide subunit antigens will usually be at least about 5 amino acids in length in order to encode an epitope, and preferably at least about 10-15 amino acids in length. There is no critical upper limit to the length of the subunit antigen, which could comprise the entire viral glycoprotein sequence, or even a fusion protein comprising the sequences of two or more of the viral glycoproteins.

The subunit antigens of the present invention can come from any suitable source. For example, the subunit antigen can comprise native gI, gIII and/or gIV glycoproteins, or fragments thereof. Subunit antigens can also be recombinant polypeptides. These recombinant subunits can take the form of partial glycoprotein sequences, full-length viral protein sequences, or even fusion proteins (e.g., with an appropriate leader for the recombinant host, or with another subunit antigen sequence for BHV-1 or another pathogen). The subunit antigen, even though carrying epitopes derived from glycoproteins, does not require glycosylation.

While it is preferred to use subunit glycoproteins containing the full-length (or near full-length) sequence of the selected BHV-1 glycoprotein, shorter sequences encoding one or more epitopes can also be employed. The truncated sequence need only encode a "polypeptide neutralizing epitope"; i.e., an epitope which elicits antibodies that neutralize virus infectivity, and/or mediate antibody-complement or antibody dependent cell cytotoxicity to provide protection of an immunized host. See, e.g., Babiuk et al. (1975) Infect. Immun. 12:958-963; Babiuk et al. (1987), supra. Particularly preferred epitopes for screening the subunit antigens will be those epitopes that are exposed on the cell membrane of infected host cells, as well as those epitopes encompassing the attachment site on intact virions. Such epitopes can be defined by monoclonal antibody analysis. See, e.g., van Drunen Littel-van den Hurk et al. (1985) Virology 144:216-227; Okazaki et al. (1987), supra.

In the vaccines of the present invention, it will generally be preferable to have more than one polypeptide neutralizing epitope in the subunit antigen(s). Furthermore, it may also be desirable to include polypeptide neutralizing epitopes from more than one glycoprotein in the subunit antigen(s). In its simplest form, this can be achieved by employing a polypeptide encoding the complete sequence of a glycoprotein (usually encompassing more than one neutralizing epitope), or by employing a combination of polypeptides encoding the sequences of two or all three of the viral glycoproteins. In a preferred embodiment employing native BHV-1 proteins, the subunit antigens would comprise, for example, gIV, a combination of gIV and gI (gIV/gI), a combination of gIV and gIII (gIV/gIII), or a combination of gI and gIII (gI/gIII), or a combination of all three glycoproteins (gI/gIII/gIV). When employing synthetic or recombinant polypeptides, the subunit antigen can be a single polypeptide encoding several neutralizing epitopes from just one of the viral glycoproteins, or several neutralizing epitopes from more than one of the viral glycoproteins (e.g., a fusion protein). Synthetic and recombinant subunit antigens can also comprise two or more discrete polypeptides encoding different neutralizing epitopes.

The subunit antigens of the present invention, particularly when they comprise short oligopeptides, may be conjugated to a vaccine carriers. Such carrier are well known in the art, such as bovine serum albumin (BSA), human serum albumin (HSA) and keyhole limpet hemocyanin (KLH). A particularly preferred carrier protein, rotavirus VP6, is disclosed in commonly owned copending U.S. patent application Ser. No. 07/092,120 and Canadian patent application Ser. No. 545,803, the disclosures of which are hereby incorporated by reference. The BHV-1 neutralizing epitopes of the present invention may also be incorporated within particle-forming viral polypeptides as a fusion protein, as described in U.S. Pat. No. 4,722,840 and EPO Pub. No. 174,759. Alternatively, the BHV-1 subunit antigens of the present invention can be incorporated into a foreign virus (e.g., vaccinia or adenovirus) as is known in the art.

The subunit antigen(s) are formulated into a vaccine composition comprising a pharmaceutically acceptable vehicle and, optionally, an adjuvant. Such formulations are well within the skill of the art. In general, the formulations will be particularly adapted for intramuscular injection, since intravenous injection is usually not practical for large-scale application to domestic animals. Alternatively, the vaccines are given orally, and the subunits formulated with a suitable oral carrier. It may be preferred to administer the vaccines of the present invention orally to raise mucosal immunity, as well as intramuscularly for systemic immunity.

A pharmaceutically acceptable vehicle, suitable for parenteral injection, is usually nontoxic and nontherapeutic. Examples of such vehicles are water, saline, Ringer's solution, dextrose solution, and Hank's solution. Nonaqueous vehicles, such as fixed oils, sesame oil, ethyl oleate, or triglycerides may also be used. Parenteral vehicles may also take the form of suspensions containing viscosity enhancing agents, such as sodium carboxymethylcellulose, sorbitol, or dextran. The vehicle will also usually contain minor amounts of additives, such as substances that enhance isotonicity and chemical stability. Examples of buffers include phosphate buffer, bicarbonate buffer and tris buffer, while examples of preservatives include thimerosal, m-or o-cresol, formalin and benzyl alcohol. Standard formulations will either be liquid injectables or solids which can be taken up in a suitable liquid as a suspension or solution for injection. Thus, in a nonliquid formulation, the vehicle may comprise dextrose, human serum albumin, preservatives, etc., to which sterile water or saline could be added prior to administration.

Various adjuvants are known in the art which can also be employed in the vaccine formulations of the present invention; e.g., Freund's adjuvant, avridine, aluminum salts [Al(OH)$_3$, AlPO$_4$, Al$_2$(SO$_4$)$_8$], Ca$_3$(PO$_4$)$_2$, saponin, DDA, Plusonics, oil-in-water emulsions (containing, e.g., avridin, dextran sulphate or vitamin E) and water-in-oil emulsions (containing, e.g., polysorbate 80). The selection of the appropriate adjuvant and its concentration in the vaccine composition is within the skill of the art.

Many protocols for administering the vaccine composition of the present invention to animals are within the skill of the art. The preferred route of administration is parenteral, particularly intramuscular. The concentration of the subunit antigen(s) in the vaccine composition is selected so that an effective dose is presented in the bovine host to elicit antibodies to the polypeptide neutralizing epitopes. Within wide limits, the dosage is not believed to be critical. Typically, the vaccine composition is administered in a manner which will deliver between about 1 to about 1,000 ug of the subunit antigen in a convenient volume of vehicle (e.g., about 1-10 ml). Preferably, the dosage in a single immunization will deliver from about 1 to about 500 ug of subunit antigen, more preferably about 5-10 to about 100-200 ug (e.g., 10-100 ug). It may also be preferred, although optional, to administer a second, booster immunization to the animal several weeks to several months after the initial immunization. To insure sustained high levels of protection against disease, it may be helpful to readminister a booster immunization to the animals once every several years.

The subunit antigen can be produced from protein recovered from virus or virus-infected cells. For example, purified virus or virus-infected cells can be disrupted or lysed and subjected to immunoadsorbent chromatography to purify gI, gIII or gIV. See, e.g., van Drunen Littel-van den Hurk et al. (1985) Virology 144:204-215. The production of monoclonal antibodies is within the skill of the art. See, e.g., van Drunen Littel-van den Hurk et al. (1984), supra; Okazaki et al. (1987), supra. Briefly, a mammal, such as a mouse, is immunized with either purified virus or the purified viral glycoprotein of interest (e.g., SDS-PAGE purified) and antibody-producing B lymphocytes recovered. Typically, these B lymphocytes are then fused with a continuous cell line to produce an immortal antibody-producing cell line; i.e., a hybridoma, trioma, etc. Immortal, antibody-producing cell lines can also be created by techniques other than fusion, such as direct transformation of B-lymphocytes with oncogenic DNA, or transfection with Epstein-Barr virus. See, e.g., M. Schreier et al., *Hybridoma Techniques* (1980); Hammerling et al., *Monoclonal Antibodies and T-Cell Hybridomas* (1981); Kennett et al., *Monoclonal Antibodies* (1980); see also U.S. Pat. Nos. 4,341,761; 4,399,121; 4,427,783; 4,444,887; 4,451,570; 4,466,917; 4,472,500; 4,491,632; 4,493,890. Native BHV-1 proteins which are immunopurified can be used in their entirety as subunit antigens, or fragments of the entire proteins containing the neutralizing epitopes can be employed as subunit antigens.

Non-native BHV-1 polypeptides can be produced by a number of methods. For example, oligopeptides containing neutralizing epitopes can be prepared synthetically by known techniques. See, e.g., U.S. Pat. No. 4,735,896. It is preferred, however, to prepare the non-native polypeptide subunit antigens by recombinant DNA methods.

Recombinant polypeptide subunit antigens are produced according to the present invention by constructing an expression cassette and transforming a host cell therewith to provide a cell line or culture capable of expressing the subunit antigen which is encoded within the expression cassette. The first step in constructing the expression cassette is to obtain a coding sequence for the glycoprotein or glycoprotein epitopes of interest. Coding sequences for gI, gIII and gIV are shown in FIGS. 5, 6 and 7. Thus, coding sequences can either be prepared directly by synthetic methods based on the disclosed sequence (or equivalent sequences encoding the same amino acids), or by using the disclosed sequence to design oligonucleotide probes to clone coding sequence using known techniques. See, e.g., Mayfield et al. (1983), supra. The coding sequence can be comprised entirely of BHV-1 glycoprotein-encoding sequences, or such glycoprotein sequences can be fused to other sequences (e.g., leader sequences) so that a fusion protein is encoded. See, e.g., U.S. Pat. Nos. 4,431,739; 4,425,437; 4,338,397. Synthetic coding sequences will also allow for the convenient construction of coding sequences which express BHV-1 glycoprotein analogs or "muteins". Alternatively, coding sequences for muteins can be prepared by site-directed mutagenesis of native BHV-1 nucleotide sequences. The techniques of site-directed mutagenesis are known in the art.

Once an appropriate coding sequence for the subunit antigen has been prepared or isolated, it can be cloned into any suitable vector or replicon. Numerous cloning vectors or replicons are known to those of skill in the art, and the selection of an appropriate cloning vector is a matter of choice. Examples of recombinant DNA vectors for cloning and host cells which can be transformed include various bacteriophage lambda vectors (*E. coli*), pBR322 (*E. coli*), pACYC171 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillis subtilis*), pBD9 (Bacillis), pIJ61 (Streptomyces), pUC6 (Streptomyces), actinophage dC31 (Streptomyces), YIp5 (Saccharomyces), YCp19 (Saccharomyces), 2-micron plasmid (Saccharomyces), and bovine papilloma virus (mammalian cells). See, generally, DNA Cloning, vols I & II, supra; Maniatis et al., supra; Perbal, supra.

To complete construction of expression cassettes, the coding sequence as described above for the subunit antigens is then operably linked to control sequences (e.g., a promoter, etc.), so that the DNA sequence encoding the subunit antigen is transcribed into messenger RNA in the host cell transformed by the expression cassette. It is within the skill of the art to operably link the subunit antigen coding sequence to appropriate control sequences in order to bring about transcription and translation. In general, the coding sequence will be downstream from the promoter sequence and any expression regulatory regions, such as enhancers or operator sequence. If the subunit antigen coding sequence is linked to a heterologous coding sequence or start codon, then it is important to place the subunit antigen coding sequence in reading frame with the latter. If the intended expression host is procaryotic, then it will also be necessary to include a ribosome binding site among the upstream control sequences. Downstream operably linked control sequences will usually comprise a transcription termination sequence, and a polyadenylation signal (for mammalian expression hosts).

When the intended expression host is a procaryotic or yeast cell, the promoter and other control sequences will necessarily be heterologous to the subunit antigen coding sequence. If the selected expression host cell is a mammalian cell, the control sequences can be homologous BHV-1 sequences, or preferably heterologous mammalian control sequences. The expression cassette can be constructed, for example, as a discrete molecular entity flanked by convenient restriction sites, or it can be constructed by inserting the coding sequence into a previously constructed expression vector with an appropriate insertion site.

A number of procaryotic expression vectors are known in the art. See, e.g., U.S. Pat. Nos. 4,440,859; 4,436,815; 4,431,740; 4,431,739; 4,428,941; 4,425,437; 4,418,149; 4,411,994; 4,366,246; 4,342,832; see also U.K. Publication Nos. GB2,121,054; GB2,008,123; GB2,007,675; and European Publication No. 103,395. The preferred procaryotic expression vectors are those for *E. coli.* Other preferred expression vectors are those for use in eucaryotic systems. Yeast expression vectors are also known in the art. See, e.g., U.S. Pat. Nos. 4,446,235; 4,443,539; 4,430,428; see also European Publication Nos. 103,409; 100,561; 96,491.

One of the preferred expression hosts of the present invention are mammalian cells. Various cell lines and expression vectors are known in the art. Examples of appropriate mammalian expression hosts include kidney cell lines (e.g., CV-1 monkey kidney cell lines), fibroblast cell lines (e.g., human, murine or chicken embryo fibroblast cell lines), Chinese hamster ovary (CHO) cells, HeLa cells, mouse NIH/3T3 and/or LMTK[31] cells. It is also known to express heterologous proteins in myeloma cell lines employing immunoglobulin promoters. See, e.g. Banerjle et al. (1983) Cell 33:729-740; U.S. Pat. No. 4,663,281. The selection of a mammalian cell line is not critical, and is within the skill of the art. Various mammalian expression vectors employing viral promoters (e.g., SV40 early region promoter, Rous sarcoma virus, LTR promoter, etc.) are also well known in the art. See, e.g., Pachl et al. (1987), supra; Gorman et al. (1982) Proc. Natl. Acad. Sci. USA 79:6777-6781; Southern et al. (1982) J. Mol. App. Genet. 1:327-341; PCT Publication No. WO87/02062. Preferred eucaryotic expression vectors are those employing the vaccinia virus, the SV40 virus, or the Rous sarcoma virus, which are also well known in the art. See, e.g., Mackett et al. (1984) J. Virol. 49:857; DNA Cloning, vol. II, pp. 191-211, supra; PCT Publication No. WO86/07593; Chakrabarty et al. (1985) Mol. Cell. Biol. 5:3403.

Another preferred embodiment of the present invention is the expression of recombinant BHV-1 polypeptides in insect cells using viral vectors, such as baculovirus. For example, high levels of expression have been achieved with vectors based on Autographa californica nuclear polyhedrosis virus (AcNPV) in Spodoptera frugiperda cells. See, e.g., Smith et al. (1983) J. Virol. 46:584-593: U.S. patent application Ser. No. 07/092,120, supra; Canadian Pat. App. Serial No. 545,803, supra.

Generally, a host cell which has been stably transformed by an expression cassette for the subunit antigen is selected to produce the recombinant polypeptide. A stably transformed host is one wherein the expression cassette has integrated into the host cell's chromosome. In the case of bacteria or yeast expression hosts, it may be preferred to select expression hosts which maintain the cassette on a non-integrating episomal element, such as a plasmid. The subunit antigen is produced by growing host cells transformed by the expression cassette under conditions which cause the expression of biologically active subunit antigen polypeptide. The appropriate conditions to bring about expression are well known in the art, and will depend primarily on the expression system and host selected. The subunit antigen polypeptide may be isolated from the host cells and purified. If the expression system secretes the subunit antigen, then the polypeptide can be purified directly from the growth media. If subunit antigen is not secreted, however, it may be necessary to disrupt the host cells and purify the subunit antigen polypeptide from the cellular lysate. Various purification techniques, such as HPLC and immunoaffinity chromatography, are known, and the selection of the appropriate purification and recovery method is within the skill of the art.

Described below are examples of the present invention which are provided only for illustrative purposes. The examples are not intended to limit the scope of the present invention in any way, as numerous embodiments within the scope of the claims will be apparent to those of ordinary skill in the art in light of the present disclosure. Those of ordinary skill in the art are presumed to be familiar with (or to have ready access to) the references cited in the application, and the disclosures thereof are incorporated by reference herein.

EXAMPLES

I

This example demonstrates the protection of cattle immunized with subunit vaccines according to the present invention.

I.A. Materials and Methods

I.A.1. Virus and Bacteria

Strains P8-2 and 108 of BHV-1 were propagated in Georgia bovine kidney cells as described previously. Babiuk et al. (1975) Infect. Immun. 12:958-963. For virus challenge of animals strain 108 was used, whereas for glycoprotein isolation the Cooper strain was used.

A culture of *Pasteurella haemolytica* (biotype A, serotype 1) was prepared as described previously. Bielefeldt Ohmann et al. (1985) J. Infect. Dis. 151:937-947. In each case, the bacterial challenge was in the log phase of growth and had a titer of 1 to $2\times10^9$ CFU/ml

I.A.2. Monoclonal Antibodies and Immunoadsorbent Purification

Monoclonal antibodies against gI, gIII, and gIV were produced as described previously. van Drunen Littel-van den Hurk et al. (1984), supra. Clones 1E11-1F6, 1D6-G11 and 1G6-2D9 which recognize gI, gIII, and gIV, respectively, were selected to prepare immunoadsorbent columns.

Purification of IgG fractions of monoclonal antibodies was carried out using protein A-Sepharose CL-4B (Pharmacia Montreal, Quebec). L'Italien in *Method of Protein Microcharacterization*, pp. 279-314 (J.E. Shively ed. 1986). Monoclonal IgG was eluted from the protein A-Sepharose column with 50 mM triethylamine and was dialyzed thoroughly against 0.1 M HEPES, pH 7.5 (coupling buffer: CB). The purified IgG was linked to activated Affigel-10 (Bio-Rad Laboratories, Mississaugo, Ontario) at 5 mg protein/ml gel, according to the manufacturer's instructions.

Glycoproteins gI, gIII, and gIV were purified from virus-infected cell lysate as previously described. van Drunen Littel-van den Hurk et al. (1985) Virology 144:216-227. Twenty-four hours postinfection, at a m.o.i. of 1, cultures were harvested and centrifuged at 1000 rpm to obtain infected cell pellets. Cells were resuspended in 1% Nonidet-P40 (NP-40) and 1% sodium deoxycholate (DOC) in 0.10 M Tris-hydrochloride, 0.15 M NaCl, (pH 7.5) and used as starting material for purification.

Immunoadsorbent columns with specificities for gI, gIII, and gIV, respectively, were prepared. After passage of the sample over the column in sample application buffer, the column was exchanged with 1 vol of fresh sample application buffer prior to washing with 2 vol of wash buffer [100 mM Tris, 500 mM NaCl, 1% NP-40 (pH 7.5)]. The wash buffer was displaced from the column with 2 vol of water prior to elution of the specifically bound antigen with 50 mM triethylamine. The eluted fractions were monitored by removing 5-50 uV collected fraction and performing a nonquantative Bradford assay. Those fractions that contained protein were then directly concentrated for further analysis. The column was requilibrated in sample application buffer for reuse or stored in sample application buffer plus 0.02% thimerosal. Columns prepared, used, and stored in this way have retained significant activity for almost a year.

I.A.3. Immunization and Pathogen Challenge

Purified glycoproteins were mixed with avridine (N,N-dioctadecyl-N,N-bis) (2-hydroxyethyl-propanediamine) as follows: 7 ml of glycoprotein (50 ug/ml), 2.8 ml of avridine (6 mg/ml), 30 ul of Tween 80, and 4.7 ml of Intralipid. Avridine was dissolved in ethanol prior to mixing with Tween 80 and Intralipid. The entire mixture was mixed by vortexing prior to mixing with the antigen. Groups of five animals each were immunized with a total of 100 ug of gI, gIII, and gIV individually or in various combinations in a 2-ml volume. Twenty-one days later animals were boosted and then challenged 3 weeks after booster immunization. Control unvaccinated calves were immunized with avridine (adjuvant alone). A further control group was immunized with a commercial killed virus vaccine (Triangle 3, Fort Dodge Laboratories, Iowa) as recommended by the manufacturer. Animals were bled at 10-day intervals for assessment of antibody responses.

Following immunization, animals were transported into an isolation pen and examined clinically, and rectal temperatures were recorded and blood samples were collected for various immunological assays to establish baseline immunological activity. The calves were then individually exposed to an aerosol of BHV-1, followed 4 days later with *P. haemolytica*. In each case, the aerosol was generated by a DeVilbiss Nebulizer, Model 65 (DeVilbiss, Barry, Ontario, Canada). Treatment was for 4 min in the case of the virus and 5 min with *P. haemolytica* as described previously. Bielefeldt Ohmann et al. (1985), supra.

I.A.4. SDS-PAGE, Western Blot, ELISA and ADCC

Sodium dodecyl sulfate (SDS)-polyacrylamide gel electrophoresis (PAGE) was carried out in 7.5% discontinuous slab gels under reducing conditions, as described previously. van Drunen Littel-van den Hurk et al (1984), supra; Laemmli (1970) Nature (London) 227:680-685.

The Western blotting technique was performed as described previously. van Drunen Littel-van den Hurk et al. (1984), supra. After electrophoresis, virus lysates were electrophoretically transferred to nitrocellulose sheets. Subsequently, the instructions for use of the Bio-Rad (Mississaugo, Ontario) immunoblot assay kit were followed.

In order to determine the antibody responses of cattle immunized with purified glycoproteins, the ELISA was performed essentially as described previously. van Drunen Littel-van den Hurk et al. (1984), supra. However, affinity-purified, peroxidase-conjugated rabbit antibovine IgG (Zymed) at a dilution of 1:3000 was used as the detecting antibody.

The neutralization titers of the bovine sera were determined as described previously. Babiuk et al. (1975), supra. To determine complement-enhanced neutralization, guinea pig serum (1:40 final dilution) was added to the virus-antibody mixture. The titers were expressed as the reciprocal of the highest dilution of antibody which caused a 50% reduction of plaques relative to the virus control.

ADCC assays were performed in microtiter plates as described previously. Babiuk et al. (1975), supra. The ratio of effector cells (polymorphonuclear cells) to target cells (BHV-1-infected, $^{51}$Cr-labeled GBK cells) was 50:1. Controls consisted of BHV-1-infected GBK tareet cells plus anti-BHV-1 serum or targets with polymorphonuclear cells in the absence of antibody.

I.A.6. Clinical Evaluation and Necropsy

The clinical evaluations were performed at the same time each day by two independent investigators who were uninformed about the specific treatments of the individual animals. The parameters evaluated included depression, appetite, fever, conjunctivitis, rhinitis, mouth-breathing, tracheitis, and pneumonia. In each case a score of 0 was assigned to healthy animals. Clinical scores of 1-4 were assigned to sick animals for each individual parameter as follows: 4, severe; 3, marked; 2, moderate; 1, mild. Total clinical scores for each animal are the sums of scores for each parameter.

Postmortem examinations were done on animals that died or were killed during the experiments. The nasal passages, larynx, trachea, and lungs were examined and photographed. Viral and bacterial lesions were recorded. The extent of pneumonia was assessed by a numerical method developed by Thomson et al. (1975) Canad. J. Comp. Med. 39:194-207. The pneumonic lesions in each lung lobe (except for the accessory lobe) were graded from 0 to 5 according to the amount of tissue involved. Total scores for seven lung lobes ranged from 0 to a theoretical maximum of 35 if the entire lung was affected.

I.A.7. Leukocyte Function

To study post-BHV-1-challenge leukocyte function, venous blood was collected into syringes containing citrate dextrose. The blood was centrifuged at 1000 g for 20 min, the buffy coat was collected, and the peripheral blood mononuclear leukocytes (PBL) were further purified on Ficoll-Hypaque as described previously. Bielefeldt Ohmann et al. (1985), supra. The polymorphonuclear neutrophils (PMN) were isolated from the original pellet by lysis of the erythrocytes as described previously. The viability of both PBLs and PMNs was greater than 99% as determined by trypan blue exclusion.

(i) Functional Analysis of PBL. Lectin-driven lymphocyte proliferation was assayed as described previously. Id. Briefly, $1 \times 10^5$ PBL were added into quadruplicate wells of a flat-bottomed microtiter plate (Nunc, Roskilde DK) in a final volume of 200 ul of RPMI 1640 plus 5% fetal bovine serum, 50 mM HEPES, and 25 mg gentamycin (all media components are from Grand Island Biological Co., Grand Island, N.Y.). Lectins, phytohemagglutinin (PHA), and concanavalin A (Con A, Calbiochem, La Jolla, CA) were added to the cultures. The cultures were incubated for 72 hr and labeled with [methyl-$^3$H]thymidine ($H^3$-Tdr) (Amersham Co., Oakville, Ontario) during the last 16-18 hr of incubation. The amount of radioactivity incorporated by PBLs was quantitated by liquid scintillation counting.

(ii) Functional Analysis of PMNs. Chemotaxis of PMNs was measured using microchemotaxis chambers. Gee et (al. (1983) Proc. Natl. Acad. Sci. USA 80:7215-7218. Briefly, 25 ul of the chemoattractant was added to the bottom wells of the chemotaxis chamber, whereas the top chamber wells contained 45 ul of PMNs. The chemotaxis chambers were incubated for 2 hr in a humidified $CO_2$ atmosphere at 37°. After incubation, the membranes were removed and nonmigrating cells were scraped from the upper surface. Membranes were fixed, stained with Giemsa, and examined microscopically for the presence of migrating cells. Cell counts are presented as the mean counts of three representative high-power microscope fields.

Luminol-enhanced chemiluminescence was measured by the method of Abramson et al. (1982). Briefly, $2 \times 10^7$ cells were added to vials containing 5 ml of Hank's balanced salt solution, 400 ul of opsonized zymosan, and 20 ul of luminol. Immediately upon addition of the cells, the reaction was followed over time using a Packard Picolite 6500 Luminometer (United Technologies Packard, Downers Grove, IL). Results are plotted as $CPM/10^7$ cells at the peak of the response which occurs at 45 min.

Superoxide anion generation and release were measured by the superoxide dismutase (SOD) inhibitable reduction of ferracytochrome C as described previously. Johnson et al. (1978) J. Exp. Med. 148:115-127. All samples were assayed in duplicate and in suspension in a final volume of 1 ml. The samples were incubated for 45 min at 37° C. The reaction was terminated by transferring 1 ml aliquots to an ice bath followed by centrifugation. The cytochrome c reduction was monitored on a spectrophotometer at 550 nm. The OD value was then converted to nm $O_2$/cell.

I.B. Results
I.B.1. Immune Responses to Purified Glycoproteins

The purified native BHV-1 glycoproteins were tested for their ability to induce protective immune responses in cattle. FIG. 1 indicates that within 10 days of immunization, all of the individual glycoproteins or combinations thereof induced detectable serum neutralizing titers. Following a booster immunization 21 days later, there was a further increase in the level of serum neutralizing antibodies induced by the glycoproteins. Highest responses were present in those animals immunized with gIV. In contrast, animals immunized with a commercial killed BHV-1 vaccine produced marginal antibody titers within 10 days of immunization. This antibody level decreased to preimmunization levels by 20 days after immunization. Following a second immunization with the commercial vaccine, antibody titers were boosted to approximately the level observed 10 days postimmunization with the purified glycoprotein. In no case did the placebo-vaccinated animals develop any immune responses.

To measure the specificity of the immune response, the serum from each animal was tested by an ELISA using individual glycoproteins as the antigens. Animals immunized with gI only reacted in the ELISA when gI antigen was used to coat the plate. In contrast, those animals that were immunized with gIII only reacted with gIII coated plates. Similarly, animals immunized with gIV only recognized gIV. These results also indicate, similar to FIG. 1, that the animals immunized with gIV had higher titers than did animals immunized with the other glycoproteins. To confirm that the animals only reacted with the specific glycoproteins with which they were immunized, Western blot analysis was performed using the sera from the individual animals. Animals immunized with gI, gIII, or gIV reacted only with their respective glycoproteins in immunoblot assays. These results further indicate that the animals were not accidentally exposed to a field strain of BHV-1 during the immunization period.

Figure 2:
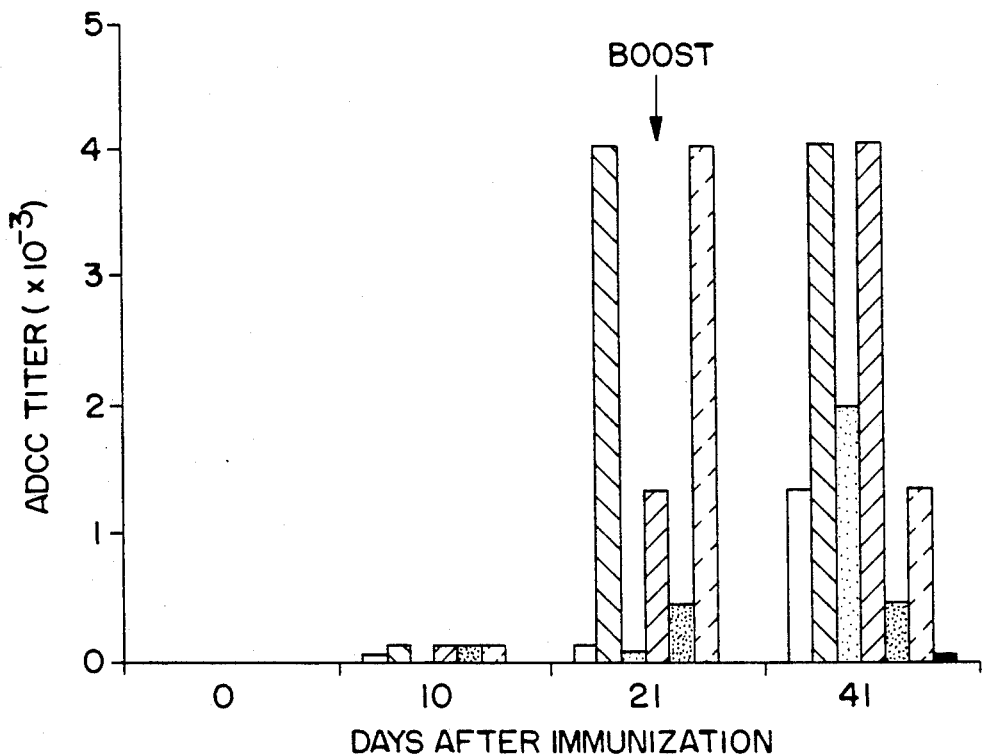
FIG. 2 shows the ADCC titers of sera obtained from calves immunized with BHV-1 glycoproteins or a commercial vaccine. The bars in the graph show the data for the various immunogens left to right as follows: gIII (open), gIV (cross-hatched), gI/gIII (small dots), gI/gIV (diagonal stripes), gIII/gIV (large dots), gI/gIII/gIV (waves), and a commercial vaccine (solid) See Example I.B.1.

Since the sera from animals immunized with glycoproteins were specific for the individual glycoproteins used for immunization and could neutralize virus infectivity in vitro, attempts were made to determine whether any one of the individual glycoproteins could induce antibody capable of participating in ADCC. The results of FIG. 2 indicate that ADCC titers, although higher than SN titers, do parallel the serum neutralizing titers. Thus, animals immunized with gIV had higher ADCC titers than did animals immunized with the other glycoproteins, those immunized with gI being marginal in killing. Again, animals immunized with the commercial killed BHV-1 vaccine exhibited a marginal response.

I.B.2. Protection Studies

Figure 3:
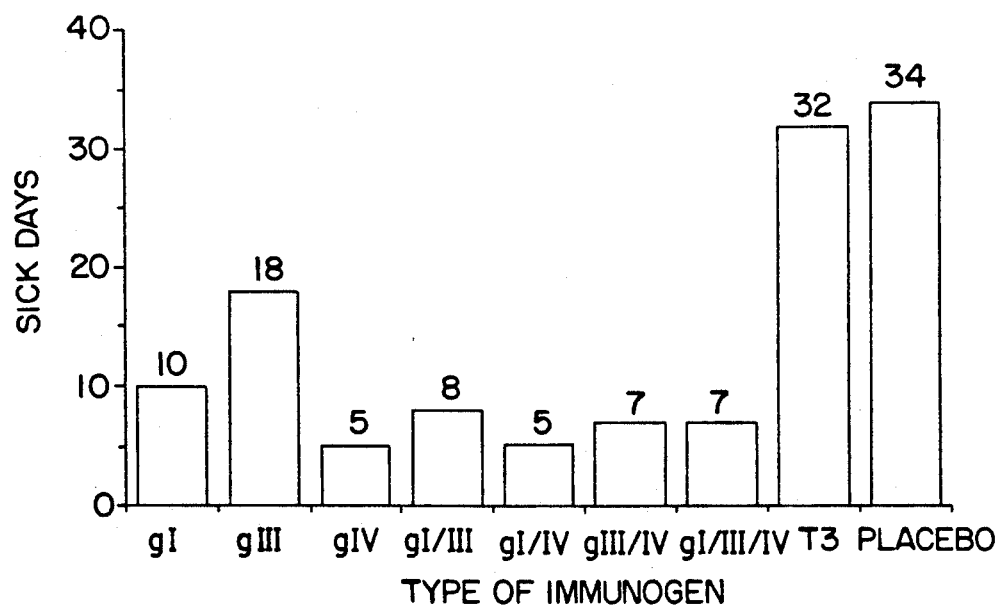
FIG. 3 shows the effect of immunization with BHV-1 glycoproteins on clinical response of calves to BHV-1/P. haemolytica challenge. T3 represents a commercial vaccine. Numbers above the bars indicate the total number of sick days (a clinical score of ten or more on any specific observation) animals in each group exhibited over a ten-day observation period. See Example I.B.2.

Prior to challenge with BHV-1 and *P. haemolytica*, all animals were healthy and had a normal rectal temperature. However, within 48 hr post-BHV-1 infection animals started exhibiting a rise in temperature. Temperature responses continued to increase until they reached peak levels 4-7 days post-BHV-1 infection. In each case, animals within the groups immunized with glycoproteins exhibited much lower temperature responses than did the placebo or animals immunized with the commercial whole virus vaccine. In addition to temperature responses, a variety of other parameters of respiratory distress were assessed. A clinical score of 10 or greater was set to indicate severe respiratory disease, which under field conditions would result in isolation of the animal and treatment to prevent pneumonia and subsequent death. FIG. 3 indicates the total number of sick days (clinical score greater than 10) for the five animals within each individual treatment group. Animals immunized with individual glycoproteins or combinations thereof exhibited fewer days of morbidity than did the whole virus- or placebo-immunized animals. All glycoprotein groups were significantly different from placebo groups. No significant difference was present between placebo and animals immunized with the commercial vaccine.

Since the individual glycoproteins provided relatively good protection against severe respiratory disease, attempts were made to determine whether intramuscular immunization with individual glycoproteins had any effect on the extent of virus shedding from the nasal passages. All five of the placebo treated animals shed virus for the entire observation period, beginning from Day 2 to Day 10 post-BHV-1 challenge. In contrast, animals immunized with the glycoproteins shed virus for a significantly fewer number of days ($P<0.005$ Fisher exact test). Once again, animals immunized with the commercial vaccine shed virus for more days than did animals immunized with individual glycoproteins (not significantly different from controls).

In the present model mortality rates of nonimmunized animals generally ranges from 40 to 80%. The mortality rate of placebo immunized animals in this particular experiment was 60%, whereas it was 40% in those immunized with the commercial vaccine. However, none of the animals immunized with the individual or glycoprotein combinations died. In an attempt to confirm that immunization with glycoproteins did induce protection and reduced lung involvement, the lungs of the animals were collected and assessed for the extent of pneumonia. The data demonstrate that the reason for the reduced morbidity of glycoprotein-immunized animals was that there was minimal infection of the lower respiratory tract. No specific glycoprotein group had more severe lung lesions or greater weight loss than the others indicating equal protection by all glycoproteins.

I.B.3. Leukocyte Functions

BHV-1 causes a significant reduction in leukocyte functions between 4 and 8 days postinfection. This immunosuppression is directly correlated to the extent of virus replication and is responsible for the secondary bacterial colonization which results in severe pneumonia. To determine the effect of immunization with various glycoproteins on macrophage functions, peripheral blood macrophages were assayed for their chemotactic response to a chemotactic agent (activated bovine serum as a putative source of C5a). Although macrophage chemotaxis was reduced in all animals, the animals immunized with the various glycoproteins had a lower degree of suppression at 5 days post-BHV-1 infection and rapidly returned to normal by 10 days postinfection. In contrast, immunosuppression was more dramatic and remained for a longer period of time in the placebo-treated animals and those immunized with the commercial vaccine. A similar pattern was observed in the case of PMNs. It is interesting to note that although there were no significant differences between the placebo and animals immunized with the commercial vaccine, these animals were actually more suppressed than was the placebo group, indicating that the vaccine does not induce significant protection from immunosuppression by BHV-1. This suggests that the level of antibody and cell-mediated immunity generated by the commercial vaccine is below protective levels. This is supported by the observation that lymphocyte blastogenesis was also suppressed in the commercial vaccine and placebo-immunized animals, whereas those immunized with any individual or combination of glycoproteins were not.

A further indication of neutrophil function was determined by measuring the ability of PMNs to produce superoxide. The PMNs from glycoprotein immunized animals produced similar levels of superoxide throughout the observation period. In contrast, the placebo group or animals immunized with a commercial vaccine had a significant reduction in their ability to produce superoxide. This reduction was a gradual decline such that by Day 10 their superoxide production capabilities were reduced to less than 30% of preinfection levels. A further indication of neutrophil function was demonstrated in a chemiluminescence assay. In this assay, instead of measuring one oxygen radical, the assay measures the ability of neutrophils to produce a number of toxic oxygen species. In this case, the glycoprotein-immunized animals did not demonstrate any significant increase in chemiluminescence for 5 days after BHV-1 infection. By 7 days post-BHV-1 infection there was an increase in chemiluminescence which began dropping by 10 days postinfection. In contrast, the placebo-treated animals and those immunized with the commercial vaccine began to have elevated chemiluminescence responses 5 days post-BHV-1 infection. These levels were extremely elevated by 7 days postinfection and began to decline by 10 days postinfection.

II

This example demonstrates the production of nonnative BHV-1 subunit antigens in recombinant vaccinia virus vectors.

II.A. Methods

II.A.1. Cells and Viruses

Strain P8-2 of BHV-1 was propagated in Georgia bovine kidney (GBK) cells and quantitated by plaquing in microtiter plates with an antibody overlay as described previously. Rouse et al. (1974) J. Immunol. 113:1391-1398. Vaccinia virus (VAC) (WR strain) and recombinant vaccinia virus was propagated in BSC-1 or BSC-40 cells. Madin Darby bovine kidney (MDBK) cells, BSC-1 and -40 cells, bovine fibroblasts (BFB), bovine tracheal cells (BTB) and human thymidine kinase-negative (TK−) 143 cells were grown as monolayers in Eagle minimal essential medium (MEM) (Grand Island Biological Co., Grand Island, N.Y.), supplemented with 10% fetal bovine serum (FBS) (Grand Island Biological Co.).

II.A.2. Preparation of DNA

All DNA used for ligations and transfections was CsCl gradient purified and set to concentrations of 1 ug/ul in 10 mM Tris [pH 7.5], 1 mM EDTA. Maniatis et al. (1984), supra.

II.A.3. Transfection and Isolation of Recombinant Viruses

Recombinant vaccinia viruses were selected by marker rescue as previously described. Wier et al. (1982) Proc. Natl. Acad. Sci. USA 79:1210–1214. Approximately $3 \times 10^6$ BSC-40 cells (thymine kinase-positive -TK$^+$) were infected with wild-type vaccinia virus (WR strain) at a multiplicity of infection (MOI) of 0.03 PFU per cell. At 4 h postinfection approximately 15 ug of CaCl$_2$—precipitated (125 mM) linearized plasmid DNA (i.e., pgB vax or pgC vax) was added to the infected BSC-40 cells. After 4 days of incubation at 37° C., viruses were harvested from cell supernatants following two cycles of freezing and thawing. Several dilutions of sonicated virus supernatants were plated on TK$^-$143 cells and then overlaid with 1% agarose in growth medium containing 5-bromo-2' deoxyuridine (25 ug/ml) to select for TK$^-$ virus. After three days individual TK$^-$plaques were removed and virus from these plaques was plated on BSC-40 cells. Putative recombinant viruses were repurified by plaquing on BSC-40 cells. Individual plaques were amplified by growth on BSC-40 cells and virus supernatants were tested for the presence of gI and gIII proteins by ELISA using polyclonal rabbit antisera specific for either gI or gIII.

II.A.4. Preparation of Radiolabeled Cell Lysates

BSC-1, MDBK. BFB or BTB cells were infected with BHV-1, VAC, VAC-I or VAC-III at an MOI of 10. After adsorption of the virus for 1 h, the monolayers were overlaid with either methionine-free or glucose-free MEM (Grand Island Biological Co.) containing 2% FBS (Grand Island Biological Co.) and further incubated at 37° C. Where applicable, tunicamycin was added, immediately after virus adsorption. Six hours after infection, 50 uCi of L-[$^{35}$S] methionine or 50 uCi of [$^{3}$H] glucosamine (Amersham, Oakville, Ont.) per ml was added to the cultures. At 24 h postinfection, the cells were harvested and washed with phosphate-buffered saline (PBS: 0.01 M NaH$_2$PO$_4$/Na$_2$HPO$_4$, 0.15 M NaCl, pH 7.4). In time course experiments, BHV-1-, VAC-, VAC-I- or VAC-III-infected BSC-1 cells were labeled with L-[35S] methionine immediately after virus adsorption and harvested at various times after infection. To increase the incorporation of isotopically labeled methionine, the cells were grown in methionine-free MEM for 6 h before infection. In pulse-chase experiments the cells were overlaid with methionine-free MEM after virus adsorption. At 6 or 12 h postinfection, the cells were pulse-labeled for 15 min with 200 uCi of L-[$^{35}$S] methionine in Hanks balanced salt solution (HBSS) (Grand Island Biological Co.). The cells were either harvested immediately or the label was first chased for 2 h by washing and incubating the cells in MEM containing 100 ug of cycloheximide per ml. To prepare lysates, the cells were suspended in modified RIPA buffer (0.02 M Tris-hydrochloride [pH 8.0], 0.15 M NaCl, 1% sodium deoxycholate, 1% Nonidet P-40), left on ice for 15 min and sonicated for 15 s at a setting of 100 on a sonifier cell disrupter (Model 1510 Braunsonic Braun, Melsunger, A.G., Germany). The suspensions were clarified by centrifugation at 20,000 rpm for 15 min in a 30° A100 rotor at room temperature (Airfuge, Beckman Instruments, Inc., Fullerton, CA). The supernatants were used immediately for immunoprecipitation as described in Example I.

II.A.5. SDS-PAGE and ELISA

Sodium dodecylsulfate-polyacrylamide gel electrophoresis (SDS-PAGE) was performed in 7.5% polyacrylamide discontinuous gels as described in Example I. Electrophoresis was carried out under reducing conditions. Samples containing $^{35}$S were analyzed by autoradiography of the gels on 3M X-ray film (Picker, Saskatoon, Sask.). Gels containing $^{3}$H were impregnated with Amplify (Amersham), dried and analyzed by fluorography at −70° C. The molecular weights of the polypeptides were estimated from the molecular weight markers (BioRad, Mississauga, Ontario) that were electrophoresed in parallel with the samples.

In order to identify recombinant vaccinia virus, expressing gI or gIII, an indirect ELISA was performed essentially as described in Example I. Microtiter plates were coated with cell extracts prepared from recombinant TK$^-$ virus-infected BSC-40 cells and reacted with gI- or gIII-specific rabbit sera. Affinity-purified, horseradish peroxidase (HRPO)-conjugated goat anti-rabbit IgG (Boehringer-Monheim, Dorval, Quebec) was used at a dilution of 1:2000 for detection.

A sandwich ELISA was used to compare the yield of glycoproteins gI and gIII from recombinant-infected cells to that from BHV-1-infected cells. Microtiter plates were coated with a mixture of monoclonal IgG as the captive antibody and then incubated with lysates from recombinant- or BHV-1-infected cells. A mixture of HRPO-conjugated monoclonal antibodies with a different epitope specificity was used for detection.

II.A.6. Cell Surface Immunofluoresence

BSC-1 cells were infected with BHV-1, VAC, VAC-I or VAC-III at an MOI of 10. After 20 h at 37° C., the cells were removed by mild trypsinization and $1 \times 10^6$ cells were resuspended in 250 ul of 1:20 diluted rabbit antiserum, specific for gI or gIII. After reaction for 45 min on ice, the cells were washed three times in HBSS and incubated with a 1:10 dilution of fluoresceinisothiocyanate-conjugated goat anti-rabbit IgG antiserum (Cappel Laboratories, West Chester, PA). After further reaction for 45 min on ice, the cells were washed three times in HBSS and finally resuspended in 10% glycerol-PBS, mounted on glass slides and observed with the aid of a fluorescence microscope.

II.B. Results

II.B.1. Construction of Vaccinia Virus Insertion Plasmids

Figure 8:
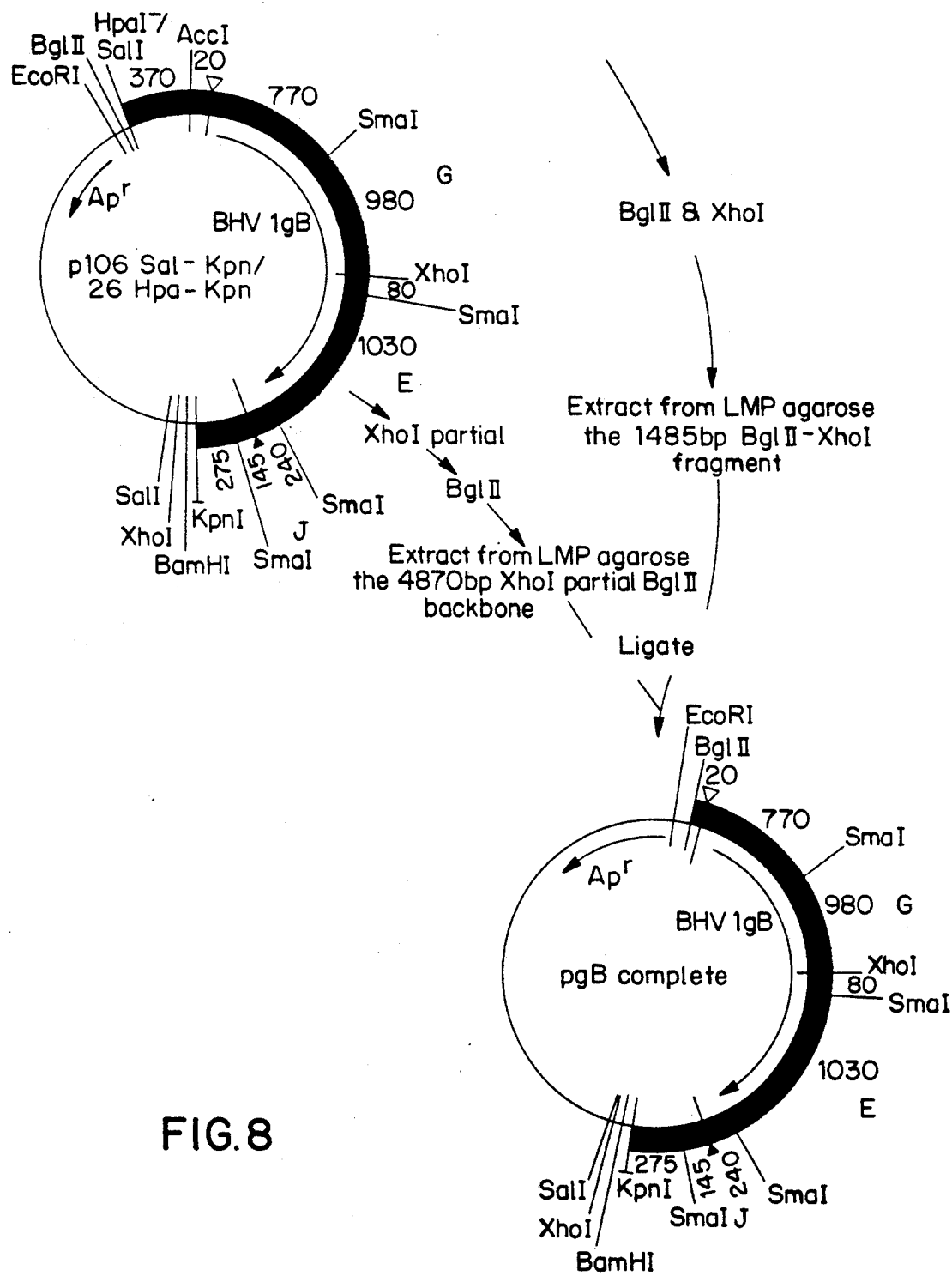
FIGS. 8 and 9 show the construction of recombinant plasmid pgBvax. The solid bar indicates BHV-1 DNA sequences. The diagonally striped bar indicates vaccinia transcriptional regulatory sequences including an RNA start site. Flanking vaccinia virus DNA sequences, including the interrupted TK gene, are shown as open bars. The single line indicates E. coli plasmid DNA. See Example II.
Figure 9:
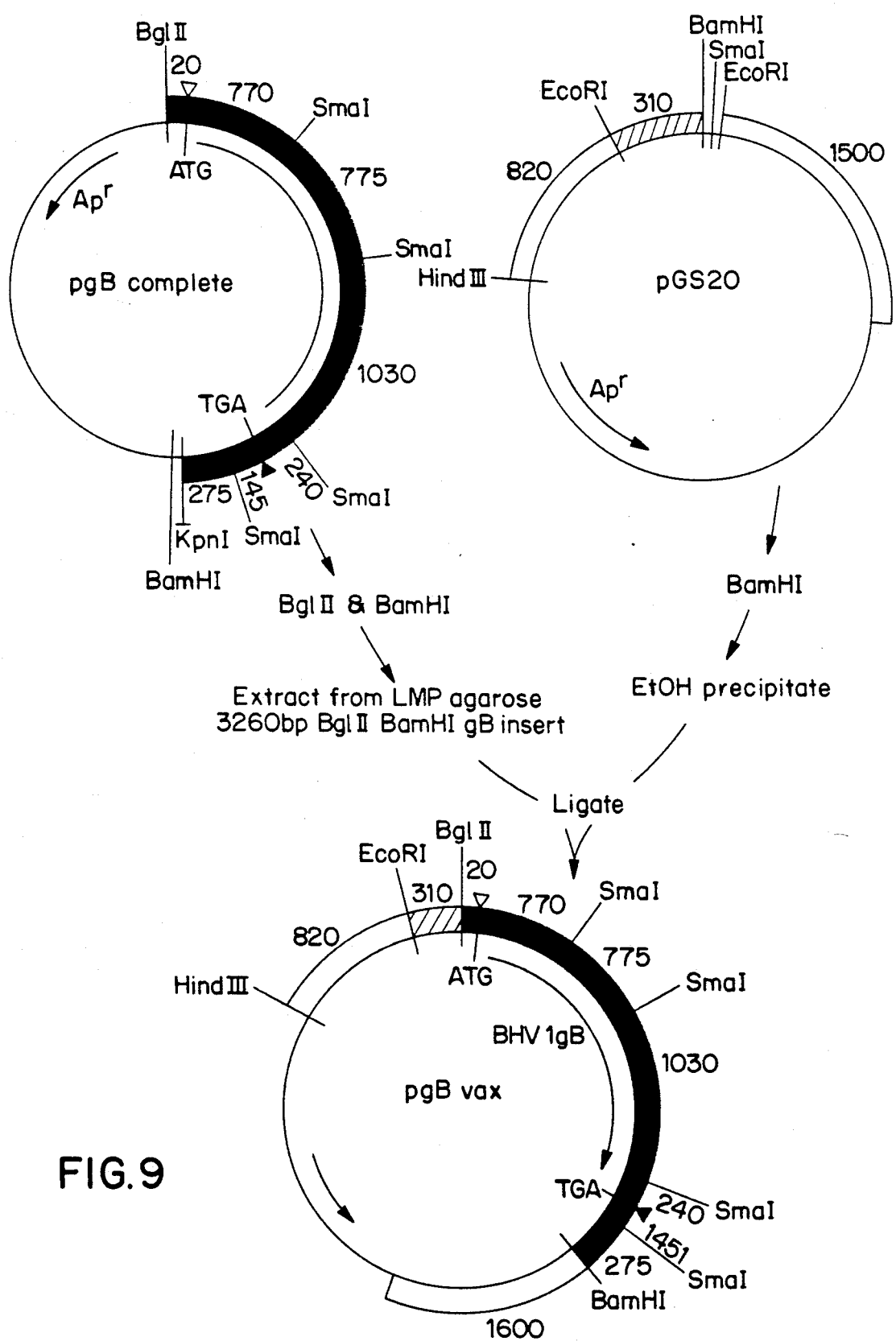

The gI gene maps between 0.422 and 0.443 genome equivalents (FIGS. 4 and 5), which is within the BHV-1 HindIII A fragment described by Mayfield et al. (1983), supra. A KpnI plus AccI partial digestion of the HindIII A fragment produces a 3255 base pair (bp) subfragment which contains the entire gI gene coding sequence. DNA sequence analyses placed an AccI site 20 bp 5' to the ATG start codon, while the KpnI site is 420 bp 3' to the TGA stop codon. This fragment was inserted into a synthetic DNA polylinker present between the EcoRI and SalI sites of PBR328 (i.e., ppo126, not shown) to produce pgB complete (FIG. 8). To this end, the AccI asymmetric end of the 3255 bp fragment was first blunted with Klenow enzyme and the gI fragment was then ligated to the HpaI plus KpnI sites of ppo126 to give pgB complete. HpaI and KpnI sites are within the polylinker of ppo126 and are flanked respectively by a BglII and a BamHI site. The gI gene was then transferred from pgB complete as a 3260 bp BglII+BamHI fragment to the BamHI site of the vaccinia virus insertion vector pGS20 (FIG. 9) to generate pgBvax (plasmid pGS20 with gI gene). Moss et al. in *Gene Ampification and Analysis*, Vol. 3, pp. 201–213 (Papas et al. eds. 1983).

Figure 10:
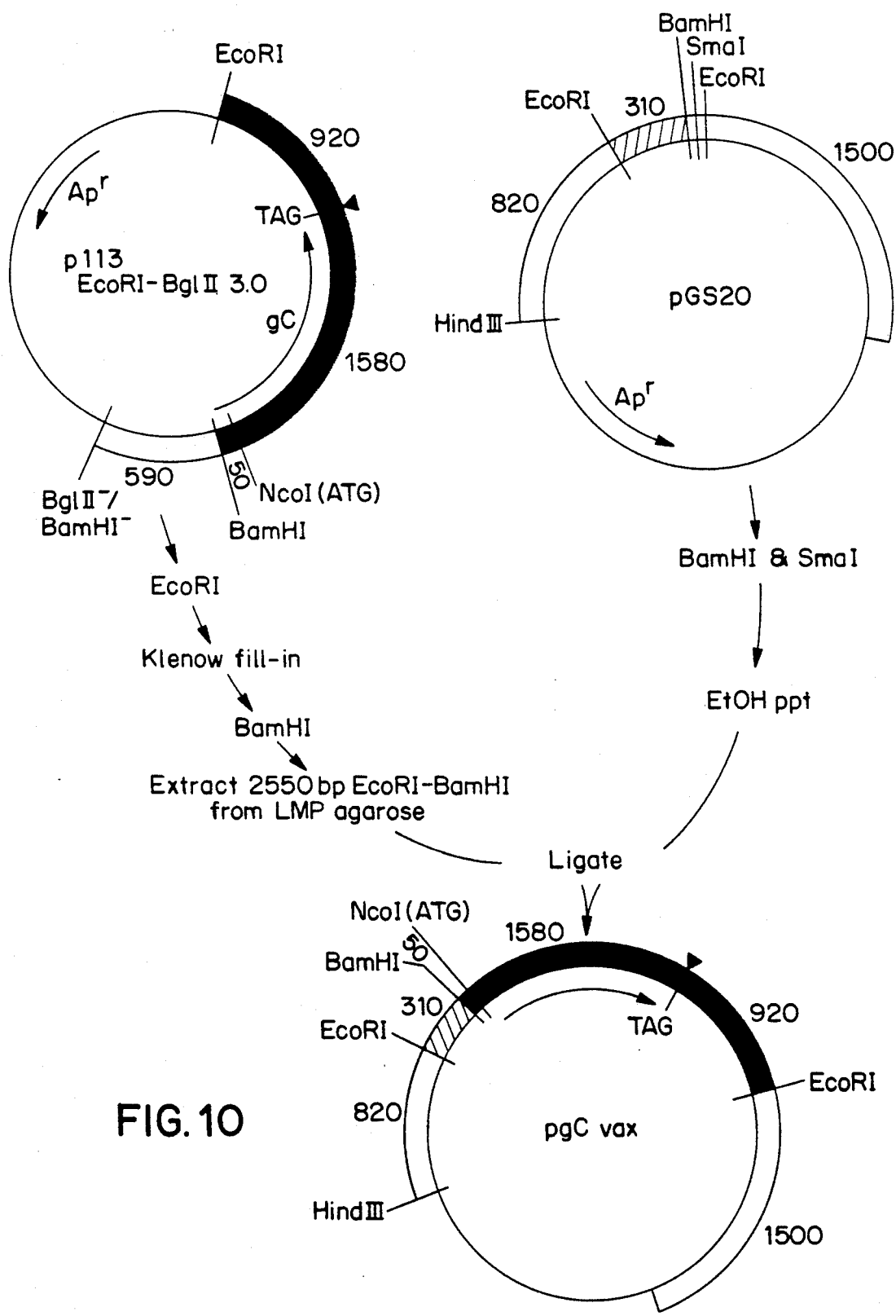
FIG. 10 shows the construction of recombinant plasmid pgCvax. The origins of the various plasmid segments are shown as described for FIGS. 8 and 9. See Example II.

The BHV-1 gIII gene maps between 0.120 and 0.131 genome equivalents (FIGS. 4 and 6) which lay within the BHV-1 HindIII I fragment. Mayfield et al. (1983), supra. The entire gene is contained within a 3090 bp BglII+EcoRI subfragment of HindIII I which was cloned into the EcoRI plus BamHI sites of ppo126 to yield p113R1 Bgl 3.0 (FIG. 10). The gIII gene was transferred to the BamHI plus SmaI sites of pGS20 as a 2550 bp EcoRI+BamHI subfragment of p113R1 Bgl 3.0 to generate pgCvax (plasmid pGS20 with gIII gene). The BamHI site of the gIII gene subfragment is 50 bp upstream from the ATG start codon while the EcoRI site which was blunted with Klenow enzyme prior to ligation is 920 bp downstream from the TAG stop codon.

II.B.2. Construction of Recombinant Vaccinia Virus

The two plasmids pgBvax and pgCvax were then used to transfect BSC-40 cells infected with wild-type vaccinia virus (WR strain). Homologous recombination between vaccinia TK sequences in the plasmid and virus genome resulted in the insertion of the gI or gIII gene into vaccinia virus. Recombinant vaccinia viruses putatively expressing BHV-1 gI or gIII were selected as TK$^-$ plaques produced on TK$^-$ 143 cells in the presence of 5-bromodeoxyuridine, following recovery of recombinant virus from the initial BSC-40 cell infection. Recombinant vaccinia virus actually expressing BHV-1 gI or gIII was identified by screening TK$^{31}$ virus in an ELISA. Infected cell extracts from recombinant TK$^-$ virus were immobilized on microtiter plates and reacted with serial dilutions of gI- or gIII-specific rabbit sera. ELISA-positive infected cell extracts were used for further studies.

II.B.3. Analysis of Recombinant Virus DNA

To insure proper gene insertion, putative recombinant virus DNA was isolated, digested with restriction endonucleases known to cut within the BHV-1 gene inserts, run on agarose gels and transferred to nitrocellulose by the methods of Southern (1975) J. Mol. Biol. 98:503. Southern transfers were then probed with $^{32}$P-labeled nick-translated gI and gIII gene fragments. The order and size of the fragments generated from the recombinant viruses were consistent with those predicted by the DNA sequence analyses of the gI and gIII genes.

II.B.4. Analysis of Glycoproteins Made in Recombinant-Infected Cells

To examine the protein products translated in vitro from the BHV-1-specific transcripts, BSC-1 cells were infected with BHV-1, WR vaccinia virus (VAC), vaccinia recombinant VAC-I or vaccinia recombinant VAC-III and labeled with L-[$^{35}$S] methionine. The radiolabeled proteins were immunoprecipitated with gI-specific monoclonal antibody 1E11 or gIII-specific monoclonal antibody 1D6, and analyzed by SDS-PAGE under reducing conditions.

Monoclonal antibody 1E11 precipitated three major glycoproteins from BSC-1 cells infected with recombinant VAC-I, but did not react with any proteins from mock-, VAC-, or VAC-III-infected cells. These glycoprotein species comigrated exactly with authentic BHV-1 glycoproteins pgIa (117K), gIb (74K) and gIc (55K). BHV-1 glycoprotein gIa, the uncleaved counterpart of gIb and gIc, was not found in recombinant VAC-I-infected cells, indicating a difference in the efficiency of processing. Glycoproteins gIa and gIb, which have apparent molecular weights of respectively 130 K and 74 K in MDBK or GBK cells, appeared to have slightly lower molecular weights of 127 K and 71 K in BSC-1 cells. Similarly, monoclonal antibody 1D6 precipitated a unique glycoprotein from BSC-1 cells infected with recombinant VAC-III, which comigrated with authentic BHV-1 glycoprotein gIII. This antibody did not react with any proteins from mock-, VAC- or VAC-I-infected cells. Although this glycoprotein has an apparent molecular weight of 91K in MDBK and GBK cells, it appeared to have a molecular weight of 85K in BSC-1 cells. The observed shifts in apparent molecular weights were probably due to a difference in the extent of glycosylation.

Several other cell lines, both permissive and non-permissive for vaccinia replication, were tested for the production of BHV-1 glycoproteins after infection by VAC I or VAC III. BFB and BTB cells, permissive for vaccinia replication, both produced the same species of BHV-1 glycoprotein, when infected with recombinant VAC-I or VAC-III. In addition to gIII, its precursor, pgIII (69 K) was detected in BHV-1-infected BFB and BTB cells, indicating that in these cells recombinant-produced gIII is processed at a faster rate than its authentic counterpart. However, in MDBK cells, which are nonpermissive for vaccinia growth, no expression of the glycoproteins was observed.

These data demonstrate that the two recombinant vaccinia viruses produce BHV-1 glycoproteins gI and gIII and their electrophoretic mobility suggests that they are fully glycosylated. In support of this conclusion, BSC-1 cells were infected with BHV-1, VAC-I, or VAC-III, labeled with [$^3$H] glucosamine and analyzed by immunoprecipitation followed by SDS-PAGE. This experiment confirmed that recombinant and authentic glycoproteins gI and gIII were glycosylated in a similar, if not identical, manner.

II.B.5. Quantitation of Glycoproteins Produced in Recombinant-Infected Cells

In order to quantitate the amounts of recombinant glycoprotein produced in different cell lines, a sandwich ELISA was performed. Cell lysates were prepared from cells infected with BHV-1, VAC-I or VAC-III and assayed with respect to production of glycoproteins gI and gIII. Table 1 shows that MDBK is the cell line of choice for producing large quantities of BHV-1 glycoproteins, followed by BTB, BFB and BSC-1 respectively. In contrast, BSC-1 is the better cell line for VAC-I and VAC-III, followed by BFB and BTB. MDBK cells infected with VAC-I or VAC-III did not produce any glycoproteins, which is in accordance with the nonpermissiveness of this cell line for vaccinia replication. A comparison of the best producing cell lines for each virus, i.e., MDBK for BHV-1 and BSC-1 for VAC-I and VAC-III, showed that authentic gI and gIII were produced in approximately a 6-fold excess over recombinant gI and gIII.

Since the highest quantities of recombinant gI and gIII, as well as sufficient amounts of authentic gI and gIII. were produced in BSC-1 cells, these cells were used for all subsequent experiments.

TABLE 1

| Virus | ELISA Titer[a] in Cell Line | | | | | | | |
|---|---|---|---|---|---|---|---|---|
| | BSC-1 | | MDBK | | BFB | | BTB | |
| | gI | gIII | gI | gIII | gI | gIII | gI | gIII |
| None | 16 | 16 | 4 | 16 | 16 | 16 | 4 | 4 |
| BHV-1 | 102 | 42 | 2000 | 1200 | 170 | 25 | 256 | 48 |
| VAC | 4 | 4 | 4 | 16 | 4 | 4 | <4 | 4 |
| VAC-I | 320 | 4 | 16 | 16 | 200 | 4 | 85 | 4 |
| VAC-III | <4 | 190 | 4 | 16 | 4 | 30 | <4 | 25 |

[a]ELISA titers were expressed as the reciprocal of the highest dilution that still gave a reading of at least 0.1.

II.B.6. Posttranslational Modifications of BHV-1 Glycoproteins

Two lines of evidence suggest that the authentic and recombinant glycoproteins gI and gIII are glycosylated to the same extent. First, they comigrated in one-dimensional polyacrylamide gels and secondly, they incorporated [$^3$H] glucosamine in an identical fashion. To support these observations, two additional experiments were performed.

The effect of tunicamycin, a drug which inhibits N-linked glycosylation, on the processing of gI and gIII was investigated. In the presence of 1 ug of tunicamycin per ml, the nonglycosylated precursor form of gI, pI (105 K) was synthesized in BSC-1 cells infected with either VAC-I or BHV-1 and immunoprecipitated by monoclonal antibody 1E11. Since the nonglycosylated precursor forms comigrated, this suggests that the polypeptide backbones of authentic and recombinant gI are identical. Consequently, the fact that the glycosylated products of VAC-I and BHV-1 also comigrated, provides further support for similar or identical glycosylation.

In the presence of 0.1 or 1.0 ug/ml of tunicamycin, a polypeptide of 77K was detected in BSC-1 cells, infected with either VAC-III or BHV-1 and immunoprecipitated with monoclonal antibody 1D6. Since gIII contains 0-linked carbohydrates, this species does not correspond to the nonglycosylated precursor, but to a partially glycosylated product, containing only O-linked carbohydrates. These species comigrated in VAC-III- and BHV-1-infected BSC-1 cells, suggesting that the N-linked and O-linked glycosylated processes are similar if not identical for both products.

The order and time course of synthesis of gI and gIII was investigated in a second series of experiments. BSC-1 cells were infected with BHV-1, VAC-I or VAC-III, labeled with L-[$^{35}$S] methionine immediately after virus adsorption and harvested at 2 h intervals after infection. Cell lysates were prepared and precipitated with monoclonal antibody 1E11 or 1D6. These experiments demonstrated that both recombinant and authentic gI were synthesized as early as 2 h postinfection. Recombinant gIII was also detected at 2 h after infection, but authentic gIII was not present until 8 h postinfection.

II.B.7. Cell Surface Expression of BHV-1 Glycoproteins

Expression of glycoproteins gI and gIII on the cell surface was examined by indirect immunofluorescence of recombinant- or BHV-1-infected live BSC-1 cells. At 20 h postinfection, the cells were incubated with either gI- or gIII-specific rabbit serum. The recombinant-derived glycoproteins had a patchy appearance over the entire cell surface, which was similar to the pattern observed for BHV-1-infected cells. The fluorescence caused by recombinant gIII was stronger than that of recombinant gI.

III

This example demonstrates the production of nonnative BHV-1 subunit antigens in recombinant SV40 and RSV vectors.

III.A. Materials and Methods

III.A.1. Reagents and Media

Restriction enzymes, T4 DNA polymerase, T4 DNA ligase, calf intestine alkaline phosphatase, phosphorylated BglII linker oligonucleotides, deoxynucleotide triphosphates and protein A-Sepharose were purchased from Pharmacia, Dorval, Quebec, Canada and used as recommended by the manufacturer. Other chemicals and reagents for DNA manipulations, transfections and protein analysis were purchased from Sigma Chemicals, St. Louis, Mo., and used according to the standard methods described by Maniatis et al. (1982), supra, and Davis et al. *Basic Methods in Molecular Biology* (1986), except where noted otherwise below. Cell culture media, fetal bovine serum (FBS), G418 and other cell culture reagents were obtained from GIBCO/BRL, Burlington, Ontario, Canada. Antibodies, wheat germ agglutinin, avidin-biotin immunoperoxidase staining kits, and other reagents for enzyme immunoassays were purchased from Dimension Laboratories, Mississauga, Ontario, Canada and used according to the manufacturers' recommendations. Radioisotopically labeled compounds and reagents for fluorography were purchased from Amersham, Oakville, Ontario, Canada.

III.A.2. Plasmid Construction

The complete coding sequence of BHV-1 gI was excised from a subclone of pSD106 (Mayfield et al. 1983, supra) and inserted into the expression vector pRSVcat (Gorman et al. 1982, supra) in place of the cat gene by ligation of the 3.3 kilobase pair (kbp) BglII-BamHI gI gene fragment into the HindIII-HpaI sites of pRSV cat after the latter sites had been converted into a unique BglII cloning site by blunt end repair, BglII linker addition, and BglII digestion (FIG. 11A). The gI gene was similarly subcloned into the expression vector pSV2neo (Southern et al. 1982, supra) in place of the neo gene by ligation of the 3.3 kbp BglII-BamHI gI gene fragment into the HindIII-SmaI sites of pSV2neo after the latter sites had been converted into a unique BglII cloning site as described for pRSVcat (FIG. 11B).

The complete coding sequence of BHV-1 gIII was excised from a subclone of pSD113 (Mayfield et al. (1983), supra) as a 2.4 kbp BamHI-EcoRI fragment treated with T4 DNA polymerase, ligated to BglII linkers, digested with BglII then cloned into pRSVcat and pSV2neo as described for BHV-1 gI (FIG. 11C and D).

Plasmid DNA was prepared for transfection by equilibrium banding in CsCl-ethidium bromide gradients and sterilized by ethanol precipitation.

III.A.3. Cells and Virus

Madin-Darby bovine kidney (MDBK) and murine 3T3 cells were cultured in Eagle's minimal essential medium supplemented with 10% FBS. Murine LMTK⁻ and L929 cells were cultured in Dulbecco modified Eagle medium (DMEM) supplemented with 5% FBS. Virus stocks of BHV-1 strain P8-2 were grown in MDBK or Georgia bovine kidney cells as previously described in Example I. Virus stocks of vaccinia virus strain WR were grown in BSC-1 cells as described in Example II.

III.A.4. Transfections

LMTK⁻ cells were transfected with expression plasmid constructions by a modified calcium phosphate precipitation procedure. LMTK⁻ cells at approximately 50% confluence were rinsed and incubated at 37° C. in fresh growth medium for 3 h before transfection. Calcium phosphate precipitates of plasmid DNA were prepared as previously described with pSV2neo DNA incorporated into each precipitate as a co-transfecting selectable marker. Graham et al. (1973) Virology 52:456-467; Wigler et al. (1979) Proc. Natl. Acad. Sci. USA 76:1373-1376. Control precipitates were prepared with pSV2neo or salmon sperm DNA only. Medium was removed from the cells and the DNA precipitates were added and adsorbed for 45 min at room temperature. Growth medium was then added and adsorption continued at 37° C. in a 4% $CO_2$ atmosphere. Chen et al. (1987) Mol. Cell. Biol. 7:2745-2757. After 4 h the medium was removed and the cells were exposed to 20% glycerol shock for 2 min at room temperature then incubated at 37° C. in growth medium supplemented with 8 mM Nabutyrate. Frost et al. (1978) Virology 91:39-50; Gorman et al. (1983) Nucleic Acids Res. 11:7631-7648. After 16-24 h the supplemented medium was removed and replaced by growth medium for 48 h. Cells were then passaged in selective growth medium containing 400 ug of G418 per ml which was replaced every 3 to 5 days. Resistant colonies appeared in 10 to 14 days at a frequency of approximately $10^{-3}$ using this method. The colonies derived from each transfection were pooled and cloned by limiting dilution at least once before screening.

III.A.5. Immunocytochemistry and Enzyme Linked Immunosorbent Assays

G418 resistant LMTK⁻ cell clones were seeded onto glass chamber slides (Miles Laboratories, Rexdale, Ontario, Canada) and 96 well plastic tissue culture plates (Nunclon, Roskilde, DK) which had been precoated with 2 ug of poly-L-lysine hydrobromide per $cm^2$, and grown to confluence. For BHV-1 infected control cells, MDBK or LMTK⁻ cells were similarly seeded onto poly-L-lysine coated slides and plates, grown to 80% confluence and then infected with BHV-1 at a multiplicity of infection of 1. After 1 h adsorption at 37° C., fresh medium containing 2% FBS was added and incubation was continued for a further 12 to 18 h, for MDBK cells, or for a few minutes, for infected LMTK⁻ cells. Transfected LMTK⁻ cell clones and control cells were either fixed and permeabilized with methanol at −20° C. for 15 min and washed in Hank's balanced salt solution (HBSS) or, for surface expression studies, washed in HBSS without fixing. Nonspecific binding sites were blocked by adding heat inactivated normal equine serum diluted 1:75 in HBSS and incubating at room temperature for 1 h. The blocking solution was removed and biotinylated wheat germ agglutinin, or monoclonal antibodies specific for gI and gIII were diluted 1:1,000 in HBSS, and added to the slides and plates, which were incubated at room temperature for 1 h. The slides and plates were then processed with an avidin-biotin enhanced immunoperoxidase assay kit specific for mouse IgG (Vector Laboratories, Burlingame, CA) according to the manufacturer's recommendations up to the final substrate development step. For slides, the final substrate was 50 mM Tris hydrochloride, pH 7.5, 0.01% $H_2O_2$, 1.7 mM $NiCl_2$, and 1 mg 3,3'-diaminobenzidine tetrahydrochloride per ml. The substrate reaction was stopped after 5 min incubation at room temperature by rinsing the slides in tap water. For enzyme linked immunosorbent assays (ELISAs) the final substrate was 0.1 M citric acid, pH 4.0, 0.015% $H_2O_2$, and 1 mg ABST (2,2'-amino-di-[3-ethylbenzthiazoline sulfonate(6)] per ml. The ELISA substrate reactions were stopped after 5 to 10 min incubation at room temperature by addition of sodium dodecyl sulfate (SDS) to a final concentration of 5% and the absorbance of each well was read at 405 nm in a microtiter plate reader.

III.A.6. Radioimmunoprecipitation

To radiolabel cellular proteins, clones or transfected LMTK⁻ cells at approximately 80% confluence were incubated in methionine free DMEM supplemented with 2% FBS at 37° C. for 6 h. For glycosylation inhibition studies, tunicamycin was included at this point at a final concentration of 2 ug per ml. After 6 h of incubation, [$^{35}$S] methionine was added to a final concentration of 50 uCi per ml and the cells were then incubated for an additional 18 h. BHV-1 infected MDBK cells were radiolabeled by a similar method as previously described. van Drunen Littel-van den Hurk et al. (1985) Virology 144:204-215.

Radiolabeled cells were harvested by scraping, washed with HBSS, and resuspended in modified RIPA buffer (50 mM Tris hydrochloride, pH 8.0, 150 mM NaCl, 1% sodium deoxycholate, 1% Nonidet P-40, 0.1% SDS and 1 mM phenylmethylsulfonyl fluoride). After incubation on ice for 15 min, the cell suspensions were sonicated then centrifuged at 75,000×g for 1 h at 4° C. The supernatants were collected, gI or gIII-specific monoclonal antibody ascites fluid were added to a final dilution of 1:20, SDS was added to a final concentration of 0.2 to 0.5%, and the samples were incubated for 16 to 18 h at 4° C. on a rocking platform. Coated protein A-Sepharose (PAS) beads were prepared by swelling lyophilized PAS beads in modified RIPA buffer at a concentration of 10 mg per ml for 1 h at 4° C. on a rocking platform then adding rabbit IgG anti-mouse IgG to a final concentration of 800 ug per ml, and incubating for a further 16-18 h. After incubation, unbound rabbit IGG anti-mouse IgG was removed from the coated PAS beads by washing three times with modified RIPA buffer. Approximately 10 mg of coated PAS beads were added to each mixture of radiolabeled cell lysate plus monoclonal antibody and the samples were incubated at 4° C. 25 on a rocking platform. After 3-4 h, the samples were washed 4 times with modified RIPA buffer then resuspended in reducing sample buffer (62 mM Tris hydrochloride, pH 6.8, 2% SDS, 5% 2-mercaptoethanol, 10% glycerol and 0.01% bromophenol blue) and boiled for 4 min. Samples were separated by electrophoresis in 10% SDS-polyacrylamide gels and fluorographed.

III.A.7. AbCC

Transfected murine clones were seeded into 96-well round-bottomed plastic tissue culture plates at a density of $2\times10^3$ cells per well and incubated at 37° C. in growth medium containing 1.5 uCi per well of $Na_2{}^{51}CrO_4$ for 24 h. The plates were washed 3 times and gI, or gIII-specific monoclonal antibodies were added at various dilutions in DMEM containing 2% FBS and 1 ug of actinomycin D per ml. The transformed cells, like all normal nucleated cells, are resistant to complement attack in the absence of metabolic inhibitors such as actinomycin D. After 2 h incubation at 37° C., freshly thawed rabbit complement (Cedar Lane, Hornby, Ontario, Canada), at various dilutions, was added. Control wells for calculation of total releasable radiolabel received 3% Triton X-100 instead of complement. After 90 min incubation at 37° C., 50% of the supernatant fluid from each well was harvested, counted and the specific release was calculated as previously described. Misra et al. (1982), supra.

III.A.8. Cytotoxic T Cell Cytotoxicity (CTCC)

C3H/HeJ ($H$-$2^k$) or Balb/c ($H$-$2^d$) mice were immunized intraperitoneally with approximately $10^8$ PFU of BHV-1 at 8 and 11 weeks of age. Three weeks after the second immunization, the spleens were excised and cell suspensions prepared by gentle homogenization. The suspensions were treated with 0.83% ammonium chloride to remove erythrocytes, then washed, counted, viability scored, and seeded into 6-well tissue culture plates at a concentration of approximately $2\times10^6$ cells per well in RPMI 1640 medium containing 10% FBS, 25 mM HEPES and $5\times10^{-5}$ M 2-mercaptoethanol. The cells were restimulated with $2\times10^6$ PFU of BHV-1 per well and incubated at 37° C. in a humidified, 5% $CO_2$ atmosphere for 6 days.

L929 and 3T3 cells to be used as targets were suspended in RPMI medium and infected with BHV-1 or vaccinia virus at a multiplicity of infection of 5 for 1 h at 37° C. Infected targets, uninfected controls, and transfected cells were then labeled with $Na_2{}^{51}CrO_4$ for 1 h at 37° C. The labeled target cells were washed three times with RPMI medium containing 5% FBS, 25 mM HEPES, and $5\times10^{-5}$M 2-mercaptoethanol, then seeded into U-bottom microtiter plates at $10^4$ cells per well.

Restimulated effector cells were washed, counted, viability scored and added to the plates containing radiolabeled targets at various effector to target cell ratios, with quadruplicate wells for each variable. The plates were then incubated for 7 h at 37° C. in a 5% $CO_2$ atmosphere before supernatant fluids were harvested, counted and specific cytotoxicity values calculated as previously described. Lawman et al. (1980) Infec. Immun. 30:451–461.

III.A.9. Immunizations with Transfected Cells and Antibody Titrations

C3H/HeJ mice were immunized intraperitoneally with $10^{6.5}$ transfected cells suspended in 0.5 ml of HBSS, without ajuvant, at 6, 10 and 14 weeks of age. Pooled sera were obtained at 5, 8, 11 and 15 weeks of age from groups of 5 identically immunized mice. BHV-1-specific antibody levels were measured by virus neutralization and ELISA assays as described in Example I.

III.B. Results

Figure 11:
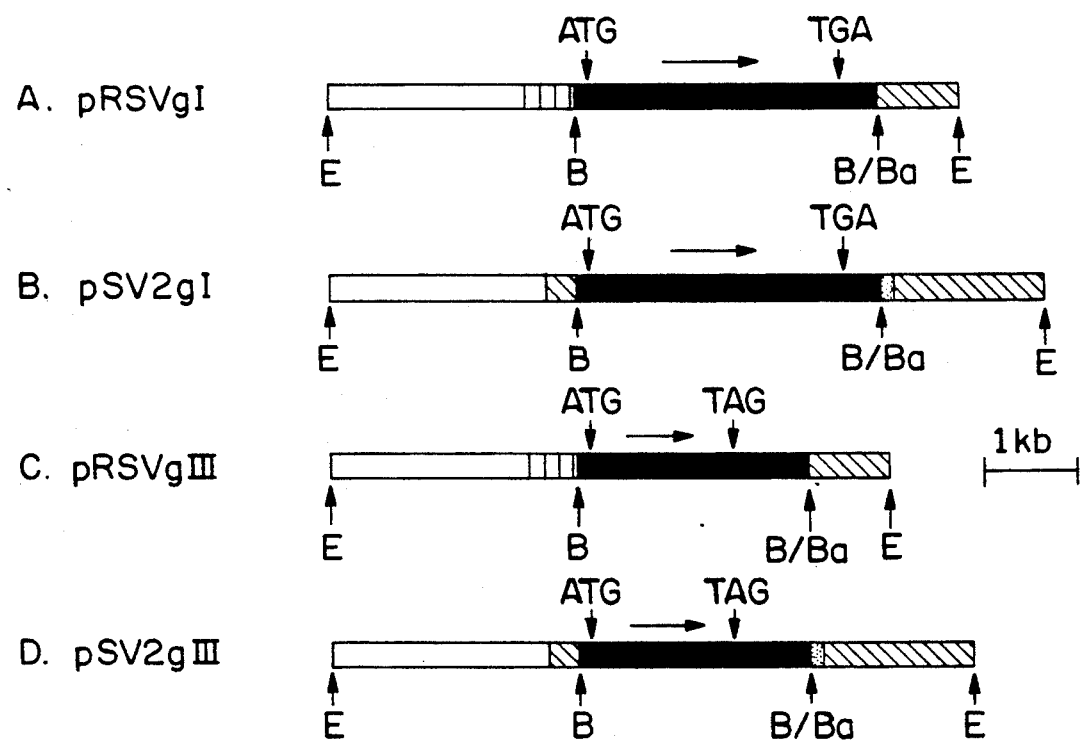
FIG. 11 shows the restriction maps for various SV40 expression vectors. The origins of the DNA sequences are represented as follows: pBR322 (open boxes), Rous sarcoma virus (vertically hatched boxes), SV40 virus (diagonally hatched boxes), BHV-1 (solid boxes) and Tn5 (stippled boxes). The start and stop codons of gI and gIII are arrowed in the direction of transcription from the Rous sarcoma and SV40 virus promoters. Restriction endonuclease cleavage sites are indicated by letters: E=EcoRI, B=BglII, B/Ba =BglII-BamHI sites destroyed by ligation. See Example III.

III.B.1. Construction of Plasmids (i) gI Constructions. The gene encoding BHV-1 gI was inserted into the eukaryotic expression vector pRSVcat in place of the cat gene such that the start codon of the gI gene was situated 100 base pairs (bp) downstream of the RSV promoter and 70 bp downstream of the transcriptional start site associated with this promoter to give pRSVgI (FIG. 11A). Yamamoto et al. (1980) Cell 22:787–797. These manipulations removed the normal viral promoter upstream of the gI gene and placed the gene under the control of the Rous sarcoma virus enhancer/promoter unit. Approximately 480 bp lay between the stop codon and the SV40 based polyadenylation signals remaining in the expression vector after removal of the cat gene. A polyadenylation signal of BHV-1 origin approximately 30 bp downstream of the gI gene stop codon was retained in this construction, however, polyadenylation signal utilization was not examined for this or any of the plasmid constructions described below. An LMTK$^-$ cell line transfected with pRSVgI was designated RSVgI.

The gI gene was also inserted into the expression vector pSV2neo in place of the neo gene such that the start codon of the gI gene was situated approximately 130 bp downstream of the SV40 early promoter and approximately 100 bp downstream of the transcriptional start site associated with this promoter to give pSV2gI (FIG. 11B). Fiers et al. (1978) Nature (London) 273:113–130. Following the gI gene stop codon were approximately 430 bp of non-coding BHV-1 DNA, 170 bp of non-coding Tn5 DNA, the sequences encoding the SV40 small t antigen intron, and the SV40 polyadenylation signals. Southern et al. (1982) J. Mol. App. Genetics 1:327–341. An LMTK$^-$ cell line transfected with pSV2gI was designated SV2gI.

(ii) gIII Constructions. The gIII gene was inserted into pRSVcat in place of the cat gene such that the gIII start codon was situated approximately 140 bp downstream of the RSV promoter and approximately 110 bp downstream of the transcriptional start site to give pRSVgIII (FIG. 11C). Approximately 850 bp lay between the gIII stop codon and the vector associated SV40 polyadenylation signals. Whether this non-coding region contained polyadenylation signals of BHV-1 origin was not examined. An LMTK$^-$ cell line transfected with pRSVgIII was designated RSVgIII.

To place the gIII gene under the control of the SV40 enhancer/early promoter region, the gIII start codon was positioned approximately 170 bp downstream of the early promoter and approximately 140 bp downstream of the transcriptional start site to give pSV2gIII (FIG. 11D). Following the gIII stop codon were approximately 800 bp of BHV-1 DNA, plus the Tn5 and SV40 sequences noted above for pSV2gI. An LMTK$^-$ cell line transfected with pSV2gIII was designated SV2gIII.

III.B.2. Expression of Recombinant gI and gIII

Approximately 120 limit diluted clones from transfections of the four expression constructions described above, plus negative control clones derived from a transfection conducted with pSV2neo alone, were screened for expression of BHV-1 gI or gIII by ELISA and immunocytochemistry assays. The use of unfixed or methanol fixed and permeabilized cells in each assay revealed surface or surface plus intracellular glycoprotein expression, respectively.

ELISAs were used to compare the relative amount of surface and intracellular gI or gIII expression by clones derived from a single transfection, and, by clones derived from transfections with the different expression vectors. For 17 clones positive for gI expression, and 35 clones positive for gIII expression, a similar range and distribution of ELISA readings was obtained with either pRSV- or pSV2-based constructions.

Immunocytochemistry revealed that expression of gI was localized predominantly intracellularly in a perinuclear region which probably corresponds to the Golgi apparatus and/or rough endoplasmic reticulum of these cells as evidenced by the identical localization of wheat germ agglutinin. However, nuclear membrane and cell surface expression of gI were also visible. In addition, clones expressing gI exhibited a high degree of cell fusion, polykaryon formation, nucleus fusion and giant cell formation which was not apparent in clones expressing gIII or negative control clones. Expression of gIII was localized predominantly in the nuclear and plasma membranes although diffuse cytoplasmic staining was also evident. The subcellular distributions of recombinant gI and gIII are similar to those observed for these glycoproteins in BHV-1-infected bovine cells, although the perinuclear accumulation of gI in the transfected murine cells appears to be greater than that observed in infected bovine cells.

III.B.3. Comparison of Recombinant gI and gIII With Native gI and qIII

Radioimmunoprecipitation of gI from BHV-1-infected bovine cells revealed three major protein bands of approximately 130,000 (130 K), 75 K and 55 K molecular weight which correspond, respectively, to the intact uncleaved glycoprotein and the two cleavable fragments which are linked by disulfide bonding in the mature nondenatured molecule. Only the latter two cleavage fragments were precipitated from two clones of murine cells transfected with gI expression plasmids, indicating that proteolytic cleavage of gI occurred to completion in these cells. In addition, the larger of the two fragments produced in the transfected murine cells was slightly lower in MW than the equivalent fragment produced in infected bovine cells. Identical results were obtained with a number of other clones positive for gI expression.

Radioimmunoprecipitation of gIII from BHV-1-infected bovine cells yielded two major bands of approximately 99 K and 73 K. These correspond, respectively, to the mature glycosylated gIII and its partially glycosylated precursor form. Only the former band was precipitated from clones of murine cells transfected with the gIII expression plasmids, suggesting that the precursor form(s) of gIII are more completely processed to mature molecules in the murine cells. As observed for gI, recombinant gIII had a slightly lower MW compared to the mature form of gIII produced in infected bovine cells. These results were also verified by analysis of a number of other clones positive for gIII expression.

Analysis of the proteins precipitated from cells treated with an N-linked glycosylation inhibitor, tunicamycin, was conducted to compare the N- and O-linked glycosylation patterns of the recombinant and infected cell glycoproteins. Radioimmunoprecipitation with gI-specific antibodies yielded a single band of approximately 105 K MW from both infected bovine cells and gI transfected murine cell clones although additional partially glycosylated products of approximately 45–50 K MW also accumulated in the transfected cells. The 105 K MW band corresponds to the nonglycosylated, uncleaved form of gI which accumulates due to the dependence of gI proteolytic cleavage on N-linked glycosylation and/or associated function(s) which are blocked by tunicamycin. The identical MW of this band in both infected bovine cells and transfected murine cells indicates that no O-linked oligosaccharides are added to gI in either cell type, and suggests that the MW differences described above for untreated cells may be due to differences in N-linked glycosylation.

Radioimmunoprecipitation of gIII from tunicamycin-treated, BHV-1-infected bovine cells yielded two bands of approximately 80 K and 57 K. These correspond to a glycosylated form of gIII, containing only O-linked oligosaccharides, and its nonglycosylated precursor. Only a 70 K band was precipitated from the tunicamycin-treated, gIII-transfected murine cell clones, suggesting that any precursor forms of gIII are rapidly processed in these cells, and that the amount of O-linked oligosaccharides added to gIII is lower compared to that added in infected bovine cells.

The antigenic structure of the recombinant gI and gIII produced in the murine cell clones was analyzed with a panel of gI- and gIII-specific monoclonal antibodies, the majority of which have been mapped to different epitopes on these glycoproteins. Relative antibody reactivity was assessed by ELISA and immunocytochemistry assays on both fixed and unifixed cells, and for selected monoclonal antibodies, by radioimmunoprecipitation and/or flow cytometry. The reactivity pattern of the entire monoclonal antibody panel was identical for the recombinant and viral forms of gI and gIII, including two gI-specific, and four gIII-specific antibodies which do not recognize denatured forms of these glycoproteins. These results suggest that the primary, secondary and/or tertiary structures of he recombinant glycoproteins, in the vicinity of the epitopes recognized by this panel of monoclonal antibodies, is indistinguishable from those of the glycoproteins produced in BHV-1-infected bovine cells.

III.B.4. AbCC and CTCC

The abCC results indicate that gI and gIII are expressed on the surface of transfected murine cell clones at a level and in a manner which is recognized by complement-fixing gI- and gIII-specific monoclonal antibodies and which thereby renders the cells susceptible to attack by complement. The lower levels of lysis of cells expressing gI is primarily due to the higher spontaneous release of radioactive label form unstable fusing cells and polykaryons.

In CTCC assays using transfected murine cell clones expressing gI or gIII as targets, splenic lymphocytes from mice immunized and restimulated with BHV-1 recognized and lysed histocompatible transfected cells expressing gI and gIII, as well as positive controls infected with BHV-1 A portion of this activity was nonspecific natural killer cell-like cytotoxicity as evidenced by the lysis of vaccinia virus-infected targets and non-histocompatible targets However, the marked restriction of cytotoxicity which occurred when nonhistocompatible target cells were used provided proof of the involvement of cytotoxic, MHC-restricted, T lymphocytes. The levels of lysis for pRSV-versus pSV2-based transfected cells does not correlate with the comparable total expression of the recombinant glycoproteins as measured by radioimmunoprecipitation and ELISA and may, therefore, reflect quantitative and/or qualitative differences in the amount of processed antigen(s) which is produced by the different transfected cell lines and recognized by the cytotoxic effector cells in this assay.

III.B.5. Immunogenicity of Transfected Cells in Mice

Histocompatible mice immunized with transfected cells in the absence of adjuvant produced detectable BHV-1-specific antibody after only one immunization. Both ELISA and virus-neutralizing antibody levels were significantly boosted by secondary but not by tertiary immunization. The induction of comparable antibody levels with cells expressing gI or gIII under the control of different enhancer/promoter units corroborates the data above which suggests that the SV40 and RSV elements are quantitatively equivalent expression units for these glycoproteins in LMTK⁻ cells. The induction of significant levels of virus-neutralizing antibody supports the reactivity and cytotoxicity data which indicate that the recombinant glycoproteins are antigenically authentic.

DEPOSIT OF BIOLOGICAL MATERIALS

The following materials were deposited with the American Type Culture Collection (ATCC), 12301 Parklawn Drive, Rockville, Md. 20852, U.S.A. These deposits will be maintained under the terms of the Budapest Treaty on the deposit of microorganisms. The nucleotide sequences of the deposited materials are incorporated by reference herein, as well as the sequences of polypeptides encoded thereby. In the event of any discrepancy between a sequence expressly disclosed herein and a deposited sequence, the deposited sequence is controlling. The deposit of the sequence is not the grant of a license to make, use or sell any of the deposited materials.

| Material | Accession Number | Deposit Date |
| --- | --- | --- |
| 1E11-1F6 | HB 9774 | July 22, 1988 |
| 1D6-G11 | HB 9775 | July 22, 1988 |
| 1G6-2D9 | HB 9776 | July 22, 1988 |
| SV2gIII | CRL 9777 | July 22, 1988 |
| SV2gI | CRL 9778 | July 22, 1988 |
| RSVgIII | CRL 9779 | July 22, 1988 |
| RSVgI | CRL 9780 | July 22, 1988 |
| VAC-I | VR 2223 | July 22, 1988 |
| VAC-III | VR 2224 | July 22, 1988 |

While the present invention has been illustrated above by certain specific embodiments, it is not intended that the specific examples should limit the scope of the invention as described in the appended claims.

We claim:

1. A method of protecting a bovine host from bovine herpesvirus type 1 (BHV-1) infection comprising:
   (a) providing a vaccine composition consisting essentially of (i) a pharmaceutically acceptable vehicle and (ii) at least one recombinant polypeptide comprising a polypeptide neutralizing epitope of a BHV-1 glycoprotein selected from the group consisting of gI, gIII, and gIV; and
   (b) administering an effective amount of said vaccine composition to said bovine host whereby neutralizing anti-BHV-1 antibodies are elicited in said bovine host.

2. The method of claim 1 wherein said vaccine composition further comprises an adjuvant.

3. The method of claim 1 wherein said BHV-1 glycoprotein is gI.

4. The method of claim 1 wherein said BHV-1 glycoprotein is gIII.

5. The method of claim 1 wherein said BHV-1 glycoprotein is gIV.

6. The method of claim 1 wherein said vaccine composition comprises at least two neutralizing epitopes form different BHV-1 glycoproteins, said different BHV-1 glycoproteins selected from the group consisting of gI, gIII and gIV.

7. The method of claim 6 wherein said two neutralizing epitopes are located on different polypeptides.

8. The method of claim 6 wherein one of said neutralizing epitopes is from gI and one of said neutralizing epitopes is from gIII.

9. The method of claim 6 wherein one of said neutralizing epitopes is from gI and one of said neutralizing epitopes is from gIV.

10. The method of claim 6 wherein one of said neutralizing epitopes is from gIII and one of said neutralizing epitopes is from gIV.

11. The method of claim 6 wherein one of said neutralizing epitopes is from gI, one of said neutralizing epitopes is from gIII, and one of said neutralizing epitopes is from gIV.

12. The method of claim 1 wherein said recombinant BHV-1 polypeptide is a recombinant polypeptide produced in a mammalian host cell.

13. The method of claim 12 wherein said mammalian host cell is transformed by a vaccinia virus vector encoding said recombinant polypeptide.

14. The method of claim 12 wherein said mammalian host cell is transformed by a SV40 vector encoding said recombinant polypeptide.

15. The method of claim 12 wherein said mammalian host cell is tranformed by a Rous sarcoma virus vector encoding said recombinant polypeptide.

16. The method of claim 1 wherein said subunit antigen is glycosylated.

17. The method of claim 1 wherein said subunit antigen is not glycosylated.

* * * * *